US012788287B2

(12) United States Patent
Wang et al.

(10) Patent No.: US 12,788,287 B2
(45) Date of Patent: Nov. 10, 2026

(54) SOLID STATE SENSOR FOR TOUCH-BASED RAPID PHYSIOLOGICAL AND CHEMICAL SENSING

(71) Applicant: THE REGENTS OF THE UNIVERSITY OF CALIFORNIA, Oakland, CA (US)

(72) Inventors: Joseph Wang, San Diego, CA (US); Jong-Min Moon, La Jolla, CA (US); Lu Yin, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 54 days.

(21) Appl. No.: 18/727,062

(22) PCT Filed: Jan. 6, 2023

(86) PCT No.: PCT/US2023/060264

§ 371 (c)(1),
(2) Date: Jul. 5, 2024

(87) PCT Pub. No.: WO2023/133530

PCT Pub. Date: Jul. 13, 2023

(65) Prior Publication Data

US 2025/0064360 A1 Feb. 27, 2025

Related U.S. Application Data

(60) Provisional application No. 63/266,513, filed on Jan. 6, 2022.

(51) Int. Cl.

| | |
|---|---|
| ***A61B 5/1486*** | (2006.01) |
| ***A61B 5/0205*** | (2006.01) |
| ***A61B 5/145*** | (2006.01) |

(52) U.S. Cl.
CPC ........ *A61B 5/1486* (2013.01); *A61B 5/02055* (2013.01); *A61B 5/14517* (2013.01)

(58) Field of Classification Search
CPC . A61B 5/1486; A61B 5/02055; A61B 5/1477; A61B 5/14507; A61B 5/277
See application file for complete search history.

(56) References Cited

U.S. PATENT DOCUMENTS 10,405,794 B2 9/2019 Begtrup et al.
11,122,982 B2 9/2021 Stubbs et al.
(Continued)

FOREIGN PATENT DOCUMENTS

EP 3097411 B1 6/2020

OTHER PUBLICATIONS

ISA, International Search Report and Written Opinion for PCT/US2023/060264, mailed on Jun. 14, 2023, 15 pages.
(Continued)

*Primary Examiner* — Carl H Layno
*Assistant Examiner* — Bryan McAllister Lee
(74) *Attorney, Agent, or Firm* — Ashurst Perkins Coie US LLP

(57) ABSTRACT

Methods, materials and devices that pertain to solid-state gel-free sensor for touch-based rapid physiological and chemical sensing are disclosed. In some embodiments of the disclosed technology, a sensor device includes a substrate, a plurality of first electrodes and a plurality of second electrodes formed over the substrate, a first current collector formed over the substrate and coupled to the plurality of first electrodes at one end of each first electrode, and a second current collector formed over the substrate and coupled to the plurality of second electrodes at one end of each second electrode, wherein the first electrodes and the second electrodes are alternately arranged, and adjacent first and second
(Continued)

electrodes are spaced apart from each other by a predetermined distance.

20 Claims, 28 Drawing Sheets

(56) References Cited

U.S. PATENT DOCUMENTS

| | | | |
|---|---|---|---|
| 2005/0084921 A1 | 4/2005 | Cranley et al. | |
| 2007/0197957 A1 | 8/2007 | Hunter et al. | |
| 2018/0220967 A1* | 8/2018 | Wang | A61B 5/1477 |
| 2018/0263539 A1 | 9/2018 | Javey et al. | |
| 2019/0059792 A1 | 2/2019 | Kane et al. | |
| 2019/0159337 A1 | 5/2019 | Wang et al. | |
| 2019/0204265 A1* | 7/2019 | Stowell | G01N 27/4146 |

OTHER PUBLICATIONS

Patton, S. et al., "Continuous Glucose Monitoring Versus Self-monitoring of Blood Glucose in Children with Type 1 Diabetes—Are there Pros and Cons for Both?," US Endocrinol, vol. 8, No. 1, 2012, 27-29.
Anhalt, H., "Limitations of Continuous Glucose Monitor Usage," Diabetes Technology & Therapeutics, vol. 18, No. 3, 2016, 115-117.
Acciaroli, G., et al., "Calibration of CGM systems," Glucose Monitoring Devices, 2020, 173-201.
Schmelzeisen-Redeker, G. et al., "Time Delay of CGM Sensors: Relevance, Causes, and Countermeasures," Journal of Diabetes Science and Technology, vol. 9, No. 5, 2015, 1006-1015.
Bandodkar, A. et al., "Tattoo-Based Noninvasive Glucose Monitoring: A Proof-of-Concept Study," Analytical Chemistry, vol. 87, 2015, 394-398.
Gao, W. et al., "Fully integrated wearable sensor arrays for multiplexed in situ perspiration analysis," Nature, vol. 529, Jan. 2016, 509-514.
Sempionatto, J. et al, "An epidermal patch for the simultaneous monitoring of haemodynamic and metabolic biomarkers," Nat. Biomed. Eng., vol. 5, Jul. 2021, 737-748.
Sharma, S. et al., "A pilot study in humans of microneedle sensor arrays for continuous glucose monitoring," Anal. Methods, vol. 10, 2018, 2088-2095.
Zhao, J. et al., "A Fully Integrated and Self-Powered Smartwatch for Continuous Sweat Glucose Monitoring," ACS Sens., vol. 4, 2019, 1925-1933.
Kim, J. et al., "Wearable non-invasive epidermal glucose sensors: A review," Talanta, vol. 177, 2018, 163-170.
Nyein, H. et al., "Regional and correlative sweat analysis using high-throughput microfluidic sensing patches toward decoding sweat," Science Advances, vol. 5, No. eaaw9906, 1-12.
Moyer, J. et al., "Correlation Between Sweat Glucose and Blood Glucose in Subjects with Diabetes," Diabetes Technology & Therapeutics, vol. 14, No. 5, 2012, 398-402.
Baker, L. et al., "Physiological mechanisms determining eccrine sweat composition," European Journal of Applied Physiology, vol. 120, 2020, 719-752.
Tang, W. et al., "Touch-Based Stressless Cortisol Sensing," Advanced Materials, vol. 33, No. 2008465, 2021, 1-11.
Sempionatto, J. et al., "Touch-Based Fingertip Blood-Free Reliable Glucose Monitoring: Personalized Data Processing for Predicting Blood Glucose Concentrations," ACS Sensors, vol. 6, 2021, 1875-1883.
Moon, J. et al., "Non-Invasive Sweat-Based Tracking of L-Dopa Pharmacokinetic Profiles Following an Oral Tablet Administration," Angewandte Chemie International Edition, vol. 60, 2021, 19074-19078.
Yin, L. et al., "A passive perspiration biofuel cell: High energy return on investment," Joule, vol. 5, 2021, 1888-1904.
Lin, S. et al., "Natural Perspiration Sampling and in Situ Electrochemical Analysis with Hydrogel Micropatches for User-Identifiable and Wireless Chemo/Biosensing," ACS Sens., vol. 5, 2020, 93-102.
Ray, T. et al., "Bio-Integrated Wearable Systems: A Comprehensive Review," Chem. Rev., vol. 119, 2019, 5461-5533.
U.S. Department of Health and Human Services, Food and Drug Administration, Center for Devices and Radiological Health, "Blood Glucose Monitoring Test Systems for Prescription Point-of-Care Use," Draft Guidance for Industry and Food and Drug Administration Staff, Nov. 2018, 1-44.
Clarke, W. et al., "Evaluating Clinical Accuracy of Systems for Self-Monitoring of Blood Glucose," Diabetes Care, vol. 10, No. 5, Sep.-Oct. 1987, 622-628.
Reiterer, F. et al., "Significance and Reliability of MARD for the Accuracy of CGM Systems," Journal of Diabetes Science and Technology, vol. 11, No. 1, 2017, 59-67.
La Count, T. et al., "Modeling Glucose Transport From Systemic Circulation to Sweat," Journal of Pharmaceutical Sciences, vol. 108, 2019, 364-371.
Bequette, B., "Continuous Glucose Monitoring: Real-Time Algorithms for Calibration, Filtering, and Alarms," Journal of Diabetes Science and Technology, vol. 4, Issue 2, Mar. 2010, 404-418.
Chamberlain, J., "Continuous Glucose Monitoring Systems: Categories and Features," American Diabetes Association, 2018, 8-10.
Nagel, K. et al., "Diabetes distress and glycaemic control in young adults with type 1 diabetes: Associations by use of insulin pumps and continuous glucose monitors," Diabetic Medicine, vol. 38, No. e14660, 2021, 1-9.
EPO, Extended European Search Report for European Patent Application No. 23737800.5 mailed Nov. 14, 2025, 13 pages.
Han, J.Y. et al., "Pt-poly(L-lactic acid) microelectrode-based microsensor for in situ glucose detection in sweat," Biosensors and Bioelectronics 170, 2020, 112675, 7 pages.
Dervisevic, M. et al., "Skin in the diagnostics game: Wearable biosensor nano- and microsystems for medical diagnostics," Nano Today 30, 2020, 100828, 23 pages.

* cited by examiner

SOLID STATE SENSOR FOR TOUCH-BASED RAPID PHYSIOLOGICAL AND CHEMICAL SENSING

CROSS-REFERENCE TO RELATED APPLICATION

This patent document is a U.S.C. § 371 National Stage application of International Application No. PCT/US2023/060264 titled "SOLID STATE SENSOR FOR TOUCH-BASED RAPID PHYSIOLOGICAL AND CHEMICAL SENSING" and filed on Jan. 6, 2023, which claims priority to and benefits of U.S. Provisional Appl. No. 63/266,513, entitled "GEL-FREE SENSOR FOR TOUCH-BASED RAPID PHYSIOLOGICAL AND CHEMICAL SENSING" and filed on Jan. 6, 2022. The entire contents of the beforementioned patent applications are incorporated by reference as part of the disclosure of this document.

TECHNICAL FIELD

The disclosed technology relates to methods and devices that pertain to solid state sensor for touch-based rapid physiological and chemical sensing.

BACKGROUND

Recent fingertip touch-based sensors enable sweat collection from the fingertip without the need for exercise or active extraction using hygroscopic porous hydrogel for analyte collection and the electrolyte that covers the electrode surfaces to enable rapid non-invasive sensing. However, such sensors still require the use of hydrogel that is prone to drying, and also contain additional problems on the sensing process due to analyte dilution and accumulation. The use of hydrogel is also difficult in its execution and storage, making the device and operation less practical and accessible for users.

SUMMARY

The disclosed technology can be implemented in some embodiments to provide methods, materials and devices that pertain to solid-state gel-free sensor for touch-based rapid physiological and chemical sensing.

In some implementations of the disclosed technology, a sensor device includes a substrate, a plurality of first electrodes formed over the substrate and extending in a first direction, a plurality of second electrodes formed over the substrate and extending in the first direction, a first current collector formed over the substrate and coupled to the plurality of first electrodes at one end of each first electrode, and a second current collector formed over the substrate and coupled to the plurality of second electrodes at one end of each second electrode, wherein the first electrodes and the second electrodes are alternately arranged in a second direction, and adjacent first and second electrodes are spaced apart from each other by a predetermined distance.

In some implementations of the disclosed technology, a sensor device includes a plurality of first electrodes and a plurality of second electrodes; a first current collector coupled to the plurality of first electrodes at one end of each first electrode; and a second current collector formed over the substrate and coupled to the plurality of second electrodes at one end of each second electrode, wherein the first electrodes and the second electrodes are alternately arranged, and adjacent first and second electrodes are spaced apart from each other by a predetermined distance.

In some implementations of the disclosed technology, a sensor device comprising a plurality of electrode arrays for simultaneous or sequential sensing of multiple biomarkers of physiological parameters, wherein each of the electrode arrays comprises: a plurality of first electrodes and a plurality of second electrodes; a first current collector coupled to the plurality of first electrodes at one end of each first electrode; and a second current collector formed over the substrate and coupled to the plurality of second electrodes at one end of each second electrode, wherein the first electrodes and the second electrodes are alternately arranged, and adjacent first and second electrodes are spaced apart from each other by a predetermined distance.

In some implementations of the disclosed technology, an array of sensors including a plurality of sensor devices, wherein the plurality of sensor devices is formed onto a substrate for sensing multiple biomarkers in a biofluid from different locations of a body simultaneously or sequentially.

In some implementations, a method includes placing a sensor device in contact with a skin of a subject, and measuring a biomarker in a biofluid from the skin of the subject using the sensor device. In some implementations, the sensor device may include a plurality of first electrodes and a plurality of second electrodes; a first current collector coupled to the plurality of first electrodes at one end of each first electrode; and a second current collector coupled to the plurality of second electrodes at one end of each second electrode, wherein the first electrodes and the second electrodes are alternately arranged, and adjacent first and second electrodes are spaced apart from each other by a predetermined distance.

The above and other aspects and implementations of the disclosed technology are described in more detail in the drawings, the description and the claims.

DETAILED DESCRIPTION

Figure 1A:
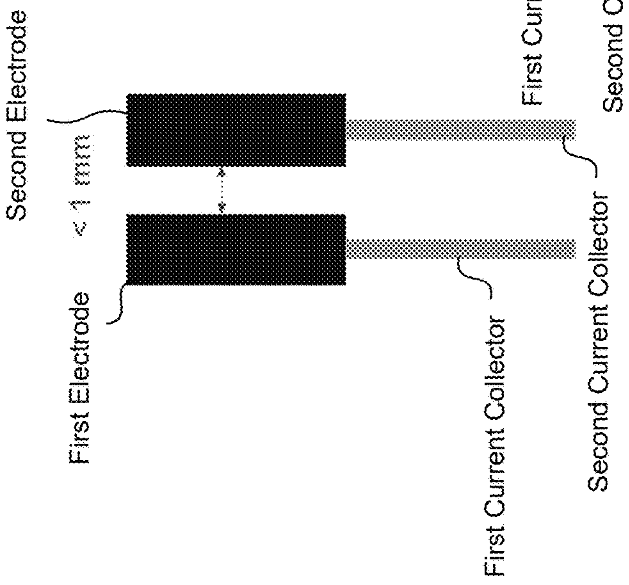
FIGS. 1A-1C show examples of a sensor that includes at least two electrodes implemented based on some embodiments of the disclosed technology.

Disclosed are methods, materials and devices that pertain to solid-state gel-free sensor for touch-based rapid physiological and chemical sensing. The disclosed technology can be implemented in some embodiments to provide a new class of non-invasive, pain-free sensors for the direct sampling and frequent measurement of the biomarker in sweat and the related physiological states, such as sweat rates. The sensor can operate with the user's direct contact using a fingertip or any other skin surfaces that emit passive, natural, thermoregulatory eccrine sweat, and measure the concentration of various ions and biomolecules in the sweat (e.g., sodium, potassium, chloride, glucose, lactate, urea, uric acid, bilirubin, hydroxybutyrate, vitamins, alcohol, levodopa, caffeine, cortisol, insulin, explosives, narcotics, nerve agents, fluoride, calcium, zinc, lead, cadmium, mercury) via electrical (e.g., conductivity, piezoresistive, thermoresistive, piezocapacitive, thermoelectric, piezoelectric), chemical (e.g., non-specific adsorption, specific binding, intercalation, insertion), or electrochemical (e.g., catalysis, redox reaction) transduction methods. The sensor uses a closely spaced or interdigitated electrode design that ensures a small inter-electrode distance (<1 mm), which enables the ionic pathway between two or more electrodes for signal transduction when in contact with the fingertip. Some embodiments of the disclosed technology can obviate the need for external analyte collection mechanisms, such as the use of hydrogels, hydrocolloids, porous materials, microfluidic channels, microneedles, iontophoresis, reverse iontophoresis, transdermal cholinergic agent delivery etc., and allows rapid, maintenance-free user-friendly near real-time biochemical and physiological sensing via direct skin contact. For this reason, the device also grants reusability and extended operation time, allowing the same sensor to be used repeatedly and frequently for users after a simple cleaning (wipe with a tissue or rinse with water).

Diabetes patients that need constant glucose monitoring use finger-pricking blood glucose meters which are highly invasive and painful. Alternative continuous glucose monitoring systems were developed, yet still requires the insertion of needles into the body for continuous sensing, which is invasive and requires maintenance. For the sensing of glucose and many other biomarkers important to human health, new wearable sensors were proposed featuring non-invasive sensing from more accessible biofluids such as sweat or interstitial fluids. The use of such epidermal sensors often requires arduous analyte extraction processes such as exercises, heat, or iontophoresis, and rely on complicated device structure, such as microfluidic devices, microneedles, iontophoretic patch etc. Such processes are intrusive, complex, and high maintenance for self-monitoring. Moreover, these devices require either a large quantity of analyte, or require special analyte uptake mechanism, such as microfluidic channels, or hydrogels, to ensure coverage of the electrode surfaces.

Recently, fingertip touch-based sensors were proposed that can enable sweat collection from the fingertip without the need for exercise nor active extraction using hygroscopic porous hydrogel for analyte collection and the electrolyte that covers the electrode surfaces to enable rapid non-invasive sensing and has been demonstrated for the sensing of various chemicals. However, this process still requires the use of hydrogel that is prone to drying, and also contain additional problems on the sensing process due to analyte dilution and accumulation. The use of hydrogel is also difficult in its execution and storage, making the device and operation less practical and accessible for users.

The disclosed technology can be implemented in some embodiments to provide a new approach for epidermal sweat sensing that obviates the need for any arduous sweat collection process such as exercises, heat, chemical stimulation or iontophoretic extraction. By using closely spaced electrodes functionalized with transducers for biomarkers, the user can perform sensing non-invasively, painless, and maintenance-free in a rapid fashion. The closely spaced or interdigitated electrode design obviates the use of hydrogel, which make the device more accessible, simple, stable, and for frequent repetitive measurements.

Figure 1B:
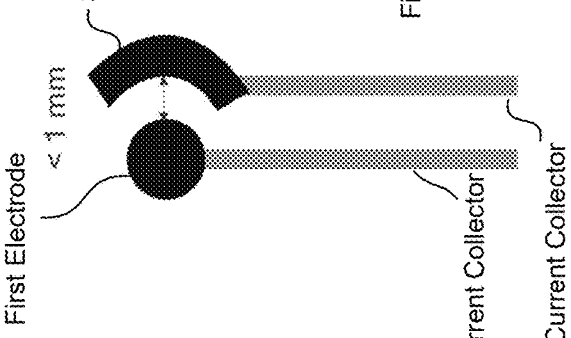
Figure 1C:
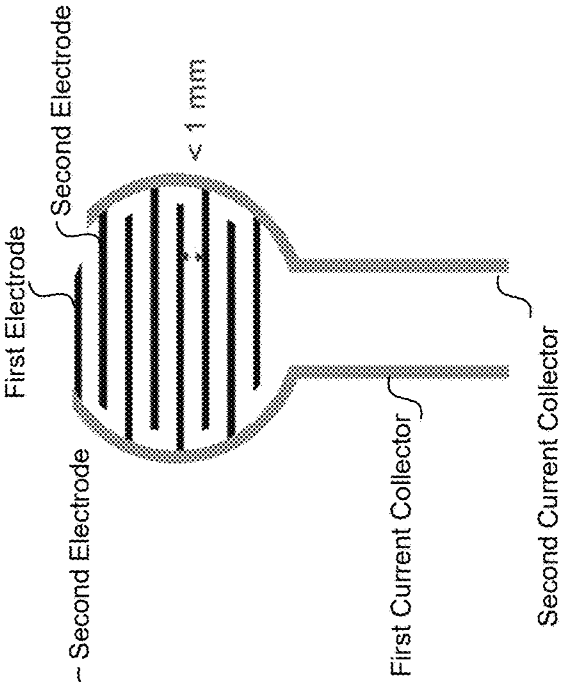
Figure 1D:
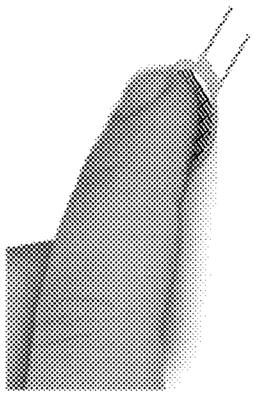
FIG. 1D shows a fingertip in contact with a sensor implemented based on some embodiments of the disclosed technology.
Figure 1E:
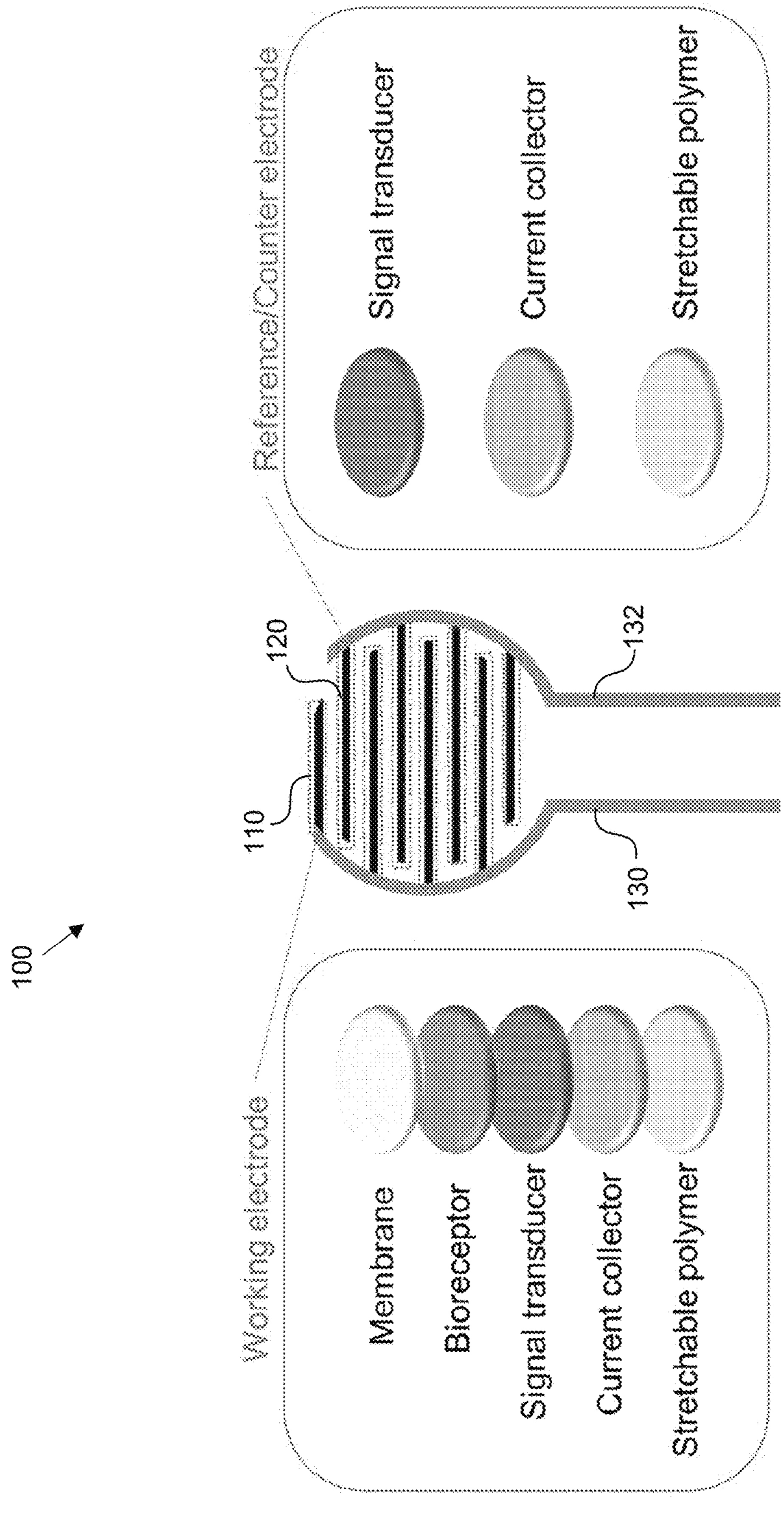
FIG. 1E shows an example of solid state gel-free sensor for touch-based rapid physiological and chemical sensing implemented based on some embodiments of the disclosed technology.
Figure 1F:
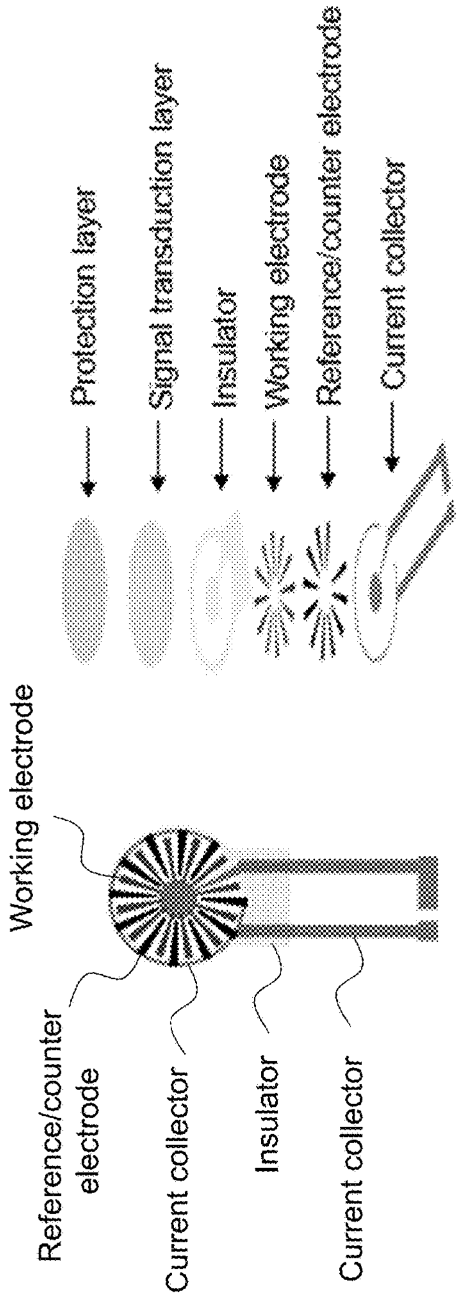
FIG. 1F shows radially-aligned interdigitated electrodes implemented based on some embodiments of the disclosed technology.
Figure 1G:
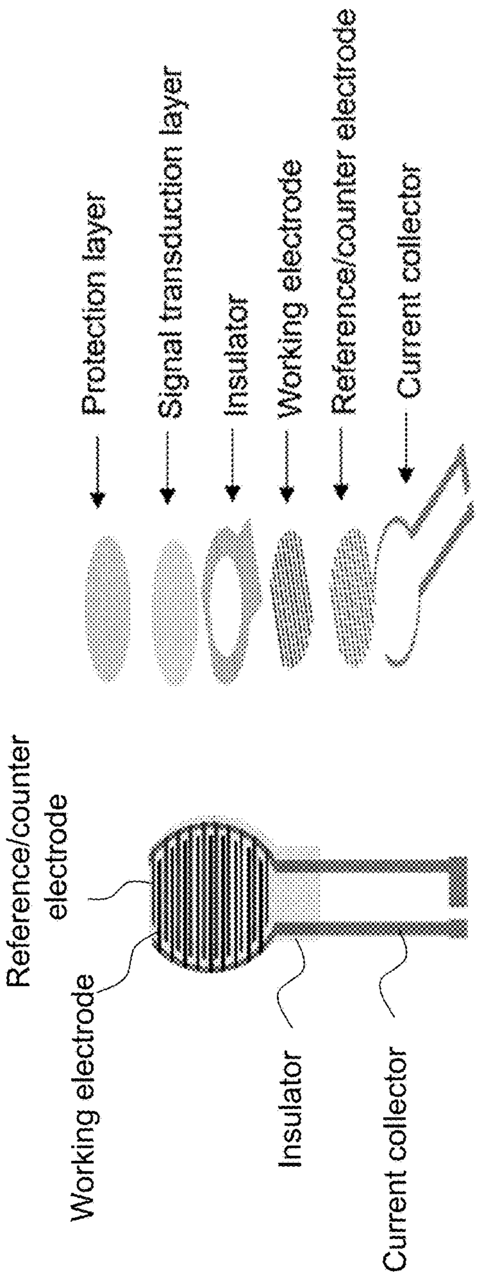
FIG. 1G shows interdigitated electrodes implemented based on some embodiments of the disclosed technology.
Figure 1H:
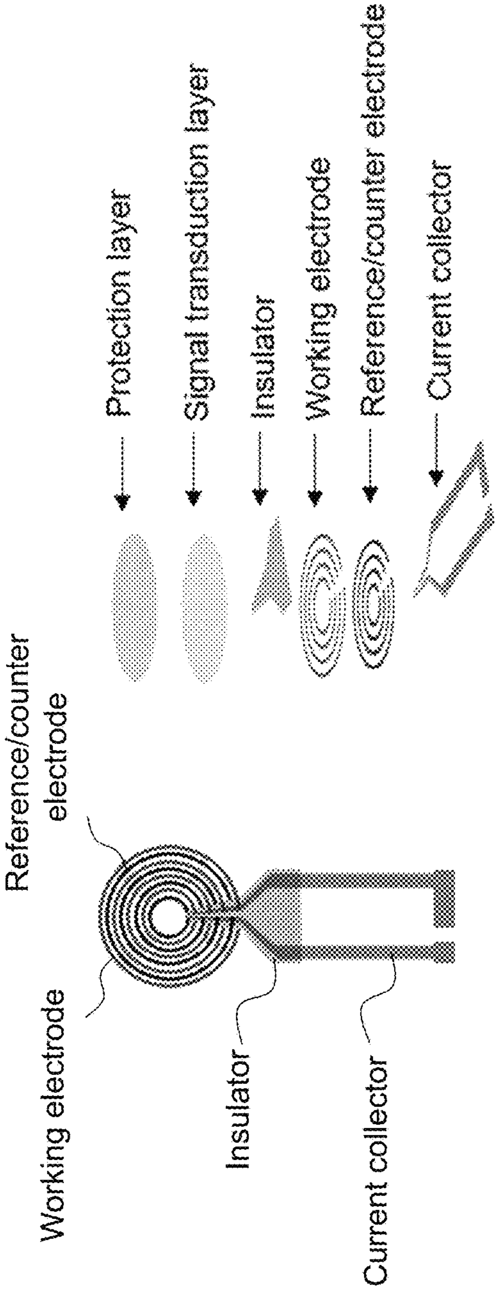
FIG. 1H shows concentric interdigitated electrodes implemented based on some embodiments of the disclosed technology.
Figure 1I:
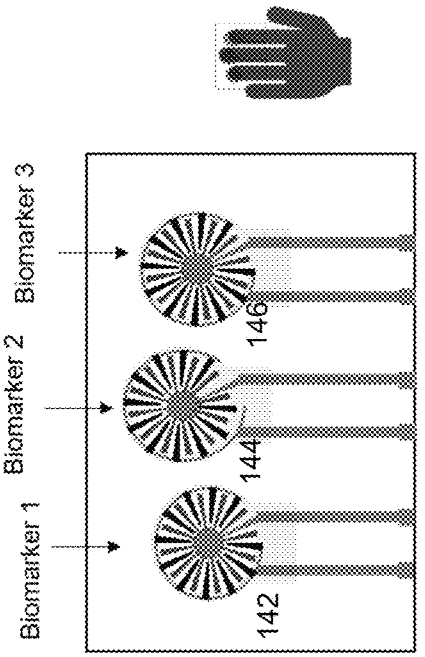
FIG. 1I shows a multiplexed array of sensors for detecting multiple biomarkers based on some embodiments of the disclosed technology.
Figure 1J:
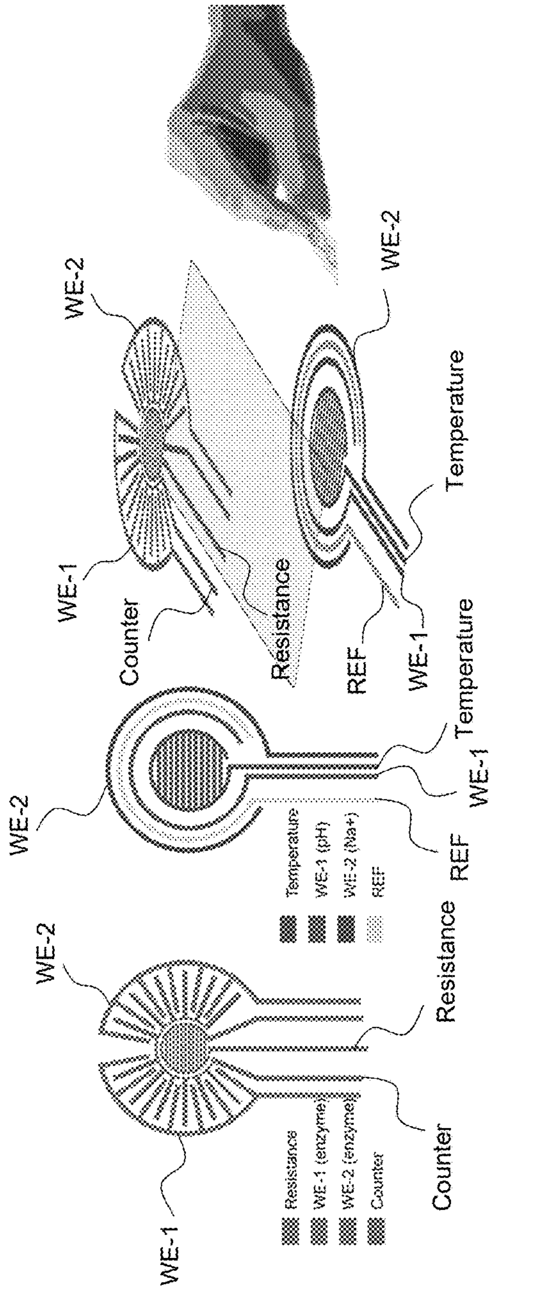
FIGS. 1J and 1K show multiplexed electrodes for detecting multiple biomarkers and physiological signals on the same sensor.
Figure 1K:
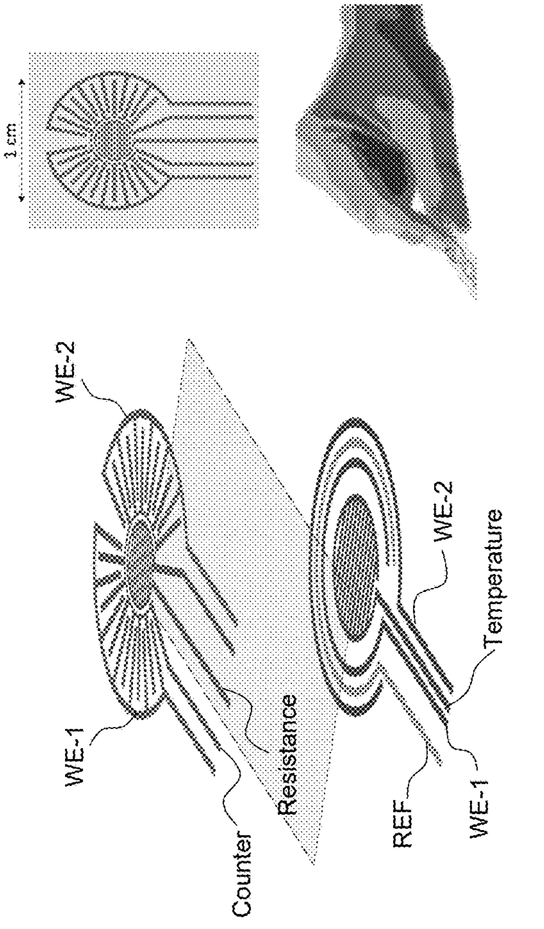
Figure 1L:
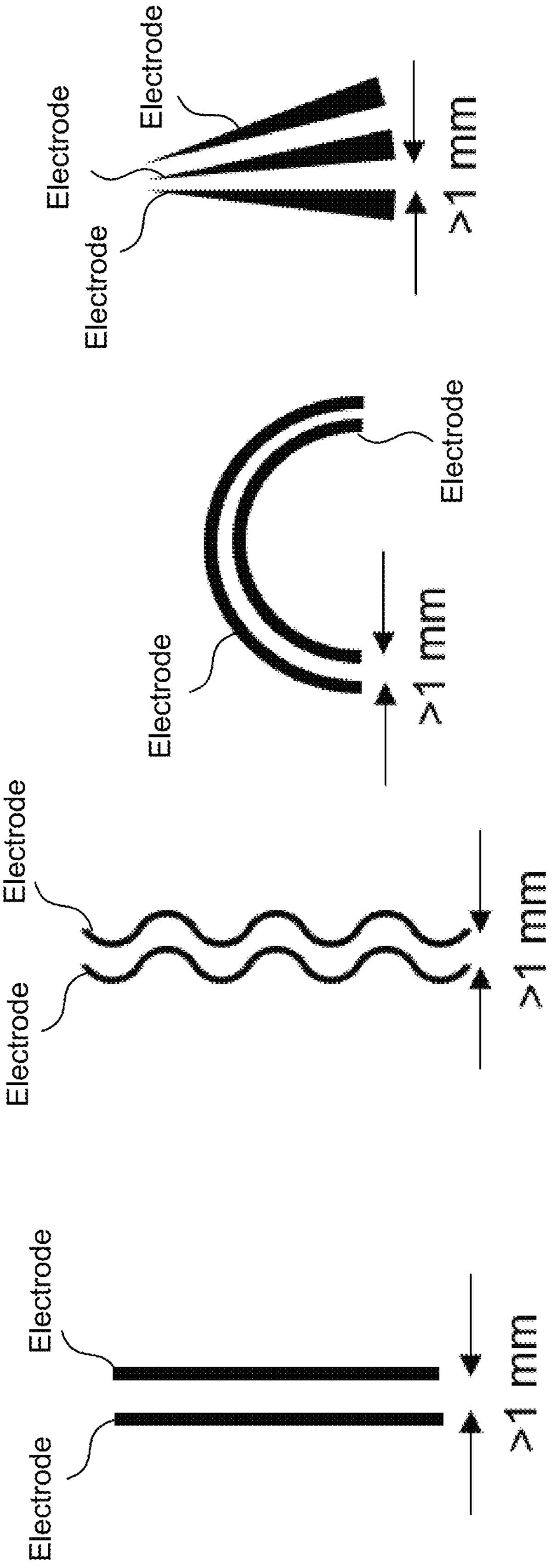
FIG. 1L shows examples of spacing between the electrodes.

FIGS. 1A-1C show examples of a sensor that includes at least two electrodes implemented based on some embodiments of the disclosed technology. FIG. 1D shows a fingertip in contact with a sensor implemented based on some embodiments of the disclosed technology. FIG. 1E shows an example of gel-free sensor for touch-based rapid physiological and chemical sensing implemented based on some embodiments of the disclosed technology. FIG. 1F shows radially-aligned interdigitated electrodes implemented based on some embodiments of the disclosed technology. FIG. 1G shows interdigitated electrodes implemented based on some embodiments of the disclosed technology. FIG. 1H shows concentric interdigitated electrodes implemented based on some embodiments of the disclosed technology. FIG. 1I shows a multiplexed array of sensors for detecting multiple biomarkers based on some embodiments of the disclosed technology. FIGS. 1J and 1K show multiplexed electrodes for detecting multiple biomarkers and physiological signals on the same sensor. FIG. 1L shows examples of spacing between the electrodes.

In some embodiments of the disclosed technology, a sensor device includes a plurality of first electrodes extending in a first direction, a plurality of second electrodes extending in the first direction, a first current collector coupled to the plurality of first electrodes at one end of each first electrode, and a second current collector coupled to the plurality of second electrodes at one end of each second electrode.

In some embodiments of the disclosed technology, the first electrodes and the second electrodes are arranged very close to each other (e.g., the distance between adjacent first and second electrodes can be smaller than 1 mm). As shown in FIG. 1A, in one example, the first and second electrodes and the first and second current collectors are arranged in the same direction. As shown in FIG. 1C, in another example, the first and second electrodes and the first and second current collectors are arranged in different directions. As shown in FIG. 1B, the first electrode has a certain shape, and the second electrode has a shape that at least partially surrounds the first electrode.

Referring to FIG. 1E, in some implementations, the first electrodes may be working electrodes, and the second electrodes may be reference/counter electrodes.

Referring to FIGS. 1F-1H, the first electrodes (e.g., working electrodes) and the second electrodes (e.g., reference/counter electrodes) are alternately arranged, and adjacent first and second electrodes are spaced apart from each other by a predetermined distance. In some implementations, the distance between adjacent first and second electrodes may be about 1 mm. In one example, the distance between adjacent first and second electrodes is smaller than 1 mm. In another example, as shown in FIG. 1L, the distance between adjacent first and second electrodes is larger than 1 mm.

In one implementation, as shown in FIG. 1F, the first electrodes (e.g., working electrodes) and the second electrodes (e.g., reference/counter electrodes) are interdigitated with one another and are arranged radially. In another implementation, as shown in FIG. 1G, the first electrodes (e.g., working electrodes) and the second electrodes (e.g., reference/counter electrodes) are interdigitated with one another and are arranged parallelly. In another implementation, as shown in FIG. 1H, the first electrodes (e.g., working electrodes) and the second electrodes (e.g., reference/counter electrodes) are arranged concentrically.

Referring to FIGS. 1F-1H, a current collector is formed, and then reference/counter electrodes are formed over the current collector, and working electrodes are formed over the reference/counter electrodes. In some implementations, an insulator is formed over the working electrodes, and a signal transduction layer is formed over the insulator, and a protection layer is formed over the signal transduction layer.

In some implementations, a sensor device includes a plurality of electrode arrays, each of which includes the first electrodes and the second electrodes discussed in this patent document. In one example, as shown in FIG. 1I, different electrode arrays 142, 144, 146 can be used to detect different biomarkers Biomarker 1, Biomarker 2, Biomarker 3.

In some implementations, as shown in FIGS. 1J and 1K, the first electrodes may include first working electrodes WE-1 and second working electrodes WE-2. In some implementations, as shown in FIGS. 1J and 1K, a sensor device may further include a reference electrode. In some implementations, as shown in FIGS. 1J and 1K, a sensor device may further include an additional sensor for measuring resistance and/or temperature.

Figure 2A:
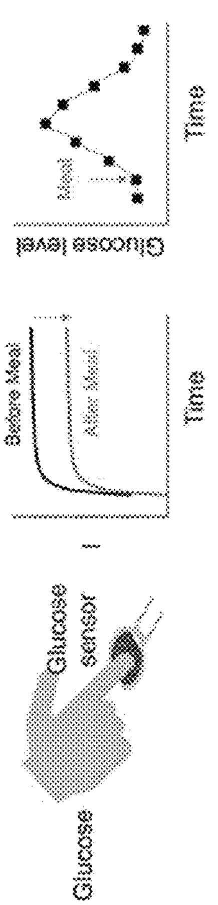
FIG. 2A shows an example of an electrode that is functionalized with glucose oxidase.
Figure 2B:
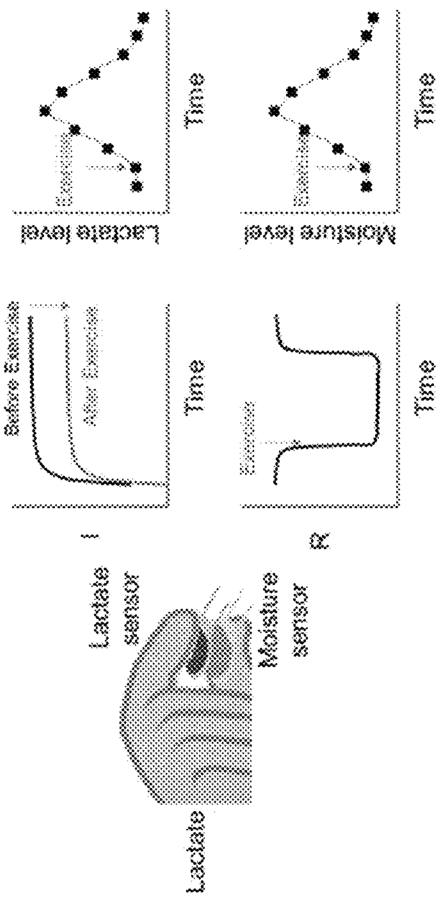
FIG. 2B shows an example of an electrode that is functionalized with lactate oxidase.
Figure 2C:
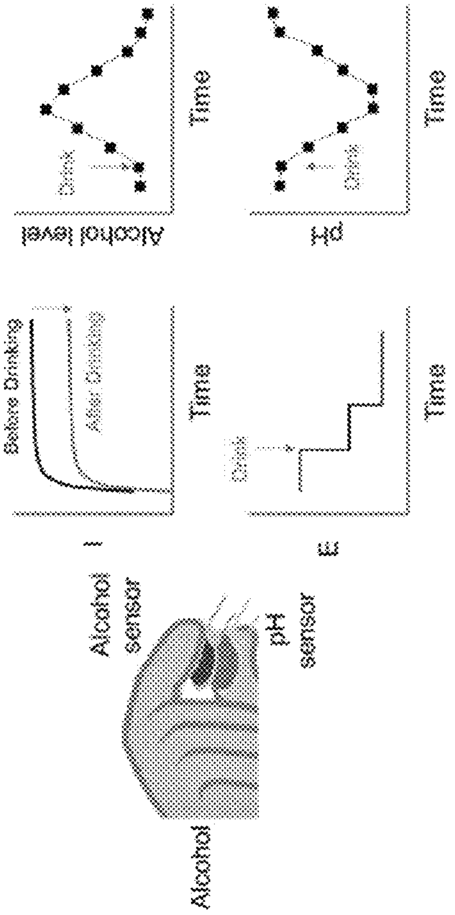
FIG. 2C shows an example of an electrode that is functionalized with alcohol oxidase.

FIG. 2A shows an example of an electrode that is functionalized with glucose. FIG. 2B shows an example of an electrode that is functionalized with lactate. FIG. 2C shows an example of an electrode that is functionalized with alcohol.

The device is a sensor composed of at least two electrodes, of which at least two of them are in a closely spaced or interdigitated configuration with a minimum distance of <1 mm from the other. The sensor includes a substrate made of glasses, silicon, paper, textile, or polymeric plastics or elastomers. The electrode can be fabricated via thin-film deposition processes such as ink-jet printing, sputtering, chemical/physical vapor deposition, thick-film deposition processes such as screen-printing, spray-coating, flexography, hydro or other additive or subtractive manufacturing processes such as computer numerical controlled milling, laser ablation, 3D printing, electrospinning. The sensor should contain a conductive electrode that can be composed of metal (e.g., Cu, Ag, Au, Pt), doped metal oxide (e.g., ITO, FTO), carbonaceous materials (e.g., graphite, graphene, reduced graphene oxide, activated carbon, carbon nanotubes, diamond), conductive polymer (e.g., PEDOT:PSS, polypyrrole, polyaniline, poly p-phenylene, polythiophene), or 2D materials (e.g., MoS2, WSe2, VO2). The electrode can be functionalized with various chemical/electrochemical transducers, such as enzymes (e.g., lactate oxidase, lactate dehydrogenase, glucose oxidase, glucose dehydrogenase, bilirubin oxidase, uricase, urea oxidase, alcohol oxidase, alcohol dehydrogenase, tyrosinase, catalase), catalysts (e.g., platinum, ruthenium, palladium, rhodium, silver), redox mediators (Prussian blue, Meldola's blue, methylene blue, indigo carmine, 2,2'-bipyridine, 1,4-naphthoquinone, tetrathiafulvalene, tetracyanoquinodimethane, ferrocene) antibodies, ion-selective membranes, silver/silver chloride mixture, molecularly imprinted membranes, or aptamers, for the sensing of biomarkers. The sensor may include additional closely spaced or interdigitated electrodes for physiological sensing, with physical transducers such as thermoresistive, thermoelectric, piezoresistive, piezocapacitive, piezoelectric, photovoltaic, physisorption, or chemisorption materials that sense physical properties such as temperature, skin moisture level, or pressure. The sensor may also include a protection layer composed of polymeric materials such as Nafion, chitosan, ethylcellulose, polyvinyl chloride. The sensor may also include an insulation layer composed of dielectric materials. The electrode layer composition can be a singular material as listed above, or a mixture or composite of the above materials.

The fabricated sensor may be used for non-invasive chemical sensing with optional complementary physiological sensing. In one example, the user can use the closely spaced or interdigitated sensor functionalized with glucose oxidase for the rapid and simple sensing of glucose in sweat, in order to establish a correlation to blood glucose level. The user can directly press the sensor for ca. 30-60 s where a potential step is applied chronoamperometric signal will be read to obtain the signal. In another example, the user can use closely spaced or interdigitated sensors made with poly(3,4-ethylenedioxythiophene) polystyrene sulfonate (PEDOT:PSS) and lactate oxidase, along with a closely spaced or interdigitated sensor made with silver to sense the sweat lactate level and the skin moisture level simultaneously, and the skin moisture data can be used to calibrate the sweat lactate signal. In another example, the user can use a closely spaced or interdigitated 3-electrode sensor functionalized in which one of the electrodes is functionalized with a pH-sensitive polyaniline polymer, and another electrode functionalized with alcohol oxidase enzyme. The user can directly press on the sensor for 30-60 s where a potential step for chronoamperometry is applied to the enzyme electrode and the open-circuit potential is monitored on the pH-sensitive electrode, and the sweat pH data and sweat alcohol signal can be obtained simultaneously, and the sweat pH data can be used to calibrate the sweat alcohol signal for improved accuracy. In these examples, the sensors may be simply reused multiple times after rapid and simple cleaning of the electrode surface via rinsing with water or wiping with tissues. For nearly real-time measurement over an extended period, the obtained data can be validated with other measurement methods such as glucometer, blood test, breathalyzer etc. and establish personal calibration to associate the thermoregulatory sweat biomarker level with biomarker level in the blood or other environment of interest.

Referring to FIG. 1E, in some implementations, a gel-free sensor 100 includes a plurality of first electrodes 110 extending in a first direction, a plurality of second electrodes 120 extending in the first direction, a first current collector 130 coupled to the plurality of first electrodes 110, and a second current collector 132 coupled to the plurality of second electrodes 120. In one example, the first electrodes 110 and the second electrodes 120 are alternately arranged in a second direction. In one example, the first direction is perpendicular to the second direction. In some implementations, the first current collector 130 is connected to one end of each first electrode 110, and the second current collector 132 is connected to one end of each second electrode 120.

In some implementations, the first electrodes 110 may be used as working electrodes, and the second electrodes 120 may be used as reference/counter electrodes. In some implementations, the first electrodes 110 may include PEDOT:PSS-Prussian blue (PB) cathode, and the second electrodes 120 may include poly(3,4-ethylene dioxythiophene) polystyrene sulfonate (PEDOT:PSS) anode. In some implementations, the first electrodes 110 and the second electrodes 120 are solid-state interdigitated electrodes (IDEs) printed on a styrene-isoprene-styrene block copolymer (SIS) substrate. In some implementations, the solid-state interdigitated electrodes (IDEs) are decorated with the glucose oxidase (GOx) enzyme that reacts selectively with the glucose in the fingertip sweat for subsequent detection. In some implementations, the first electrodes 110 and the second electrodes 120 extend in the same direction (e.g., the second direction) and alternately arranged at a predetermined distance. In one example, the predetermined distance between adjacent first electrodes 110 and second electrodes 120 provides ionic pathways. In some implementations, the predetermined distance is smaller than 1 mm.

In some implementations, the gel-free sensor 100 may further include a substrate structured to support the first and second electrodes 110, 120 and the first and second current collectors 130, 132. In one example, the substrate includes at least one of glass, silicon, paper, textile, polymeric plastic or elastomer. In some implementations, the gel-free sensor 100 may further include a glucose oxidase (GOx) enzyme layer formed over the first and second electrodes and the first and second current collectors to react selectively with a glucose in a body fluid for detection. In one example, the body fluid includes a fingertip sweat.

The disclosed technology can be implemented in some embodiments to provide a solid-state touch sensor that enables a frequent, accurate, non-invasive glucose monitoring.

Figure 3B:
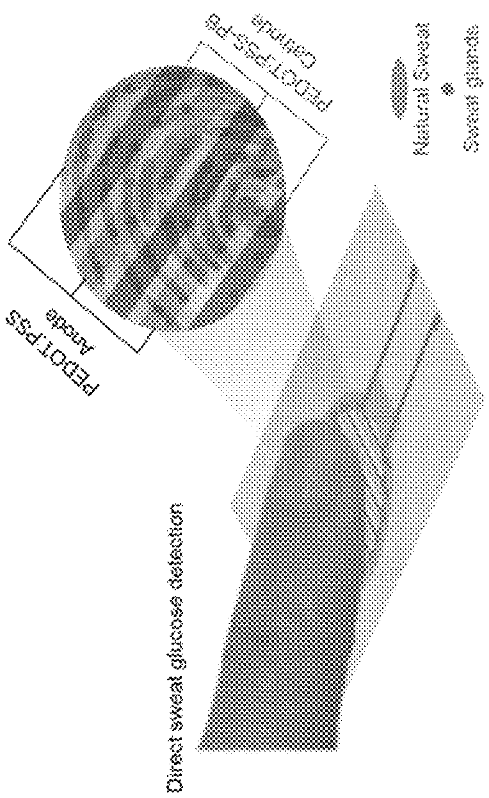
FIGS. 3A-3F show solid-state interdigitated electrodes (IDEs) for rapid glucose sensing with fingertip natural perspiration.
Figure 3A:
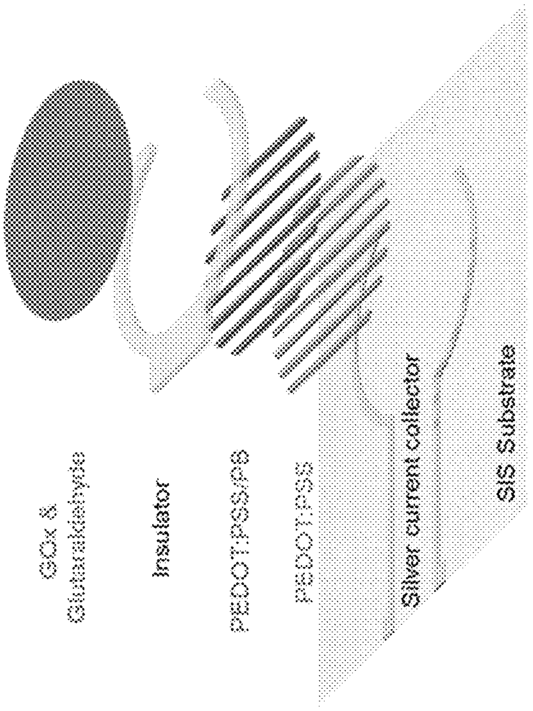
Figure 3C:
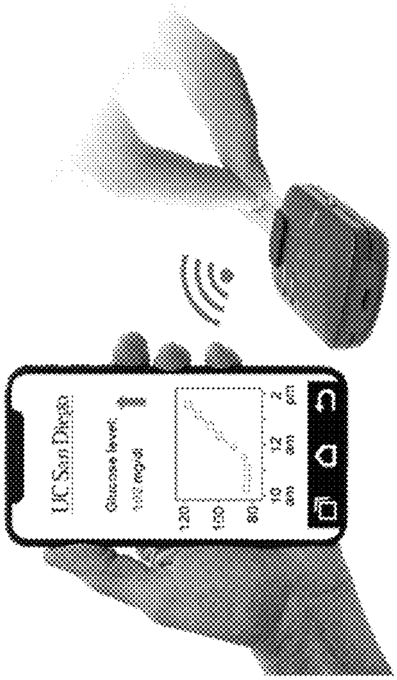
Figure 3D:
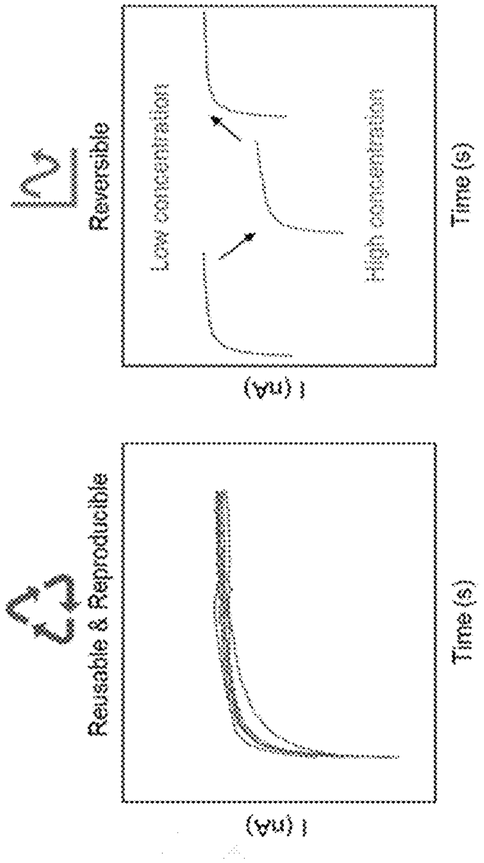
Figure 3E:
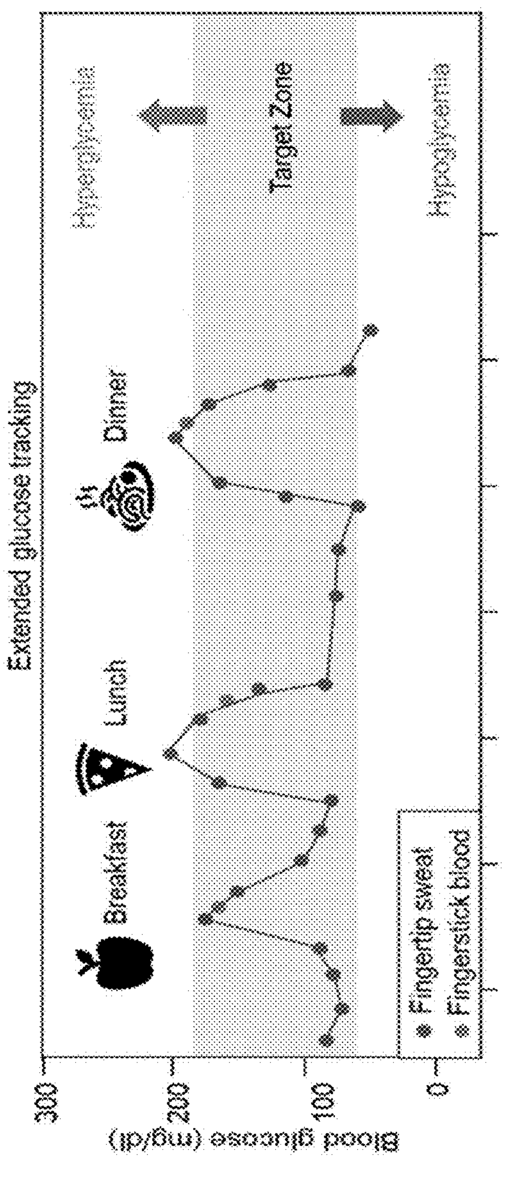
Figure 3F:
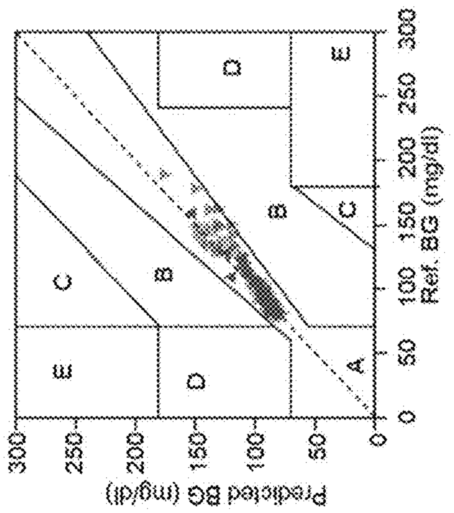

FIGS. 3A-3F show solid-state interdigitated electrodes (IDEs) for rapid glucose sensing with fingertip natural perspiration. FIG. 3A shows exploded-view schematics of the structure of the printed PEDOT:PSS-based IDE sensor. FIG. 3B is an illustration of the accumulated sweat within the grooves of the finger establishing connections between the PEDOT:PSS-PB cathode and the PEDOT:PSS anode for subsequent electrochemical reaction. FIG. 3C shows an illustration suggesting the use of the gel-free IDE sensor for rapid and frequent non-invasive sensing of glucose level during events causing glucose fluctuation. FIG. 3D shows CA curves demonstrating the reusability and reversibility of the sensor enabling repeated sensing. FIG. 3E shows an illustration suggesting the possible use of the gel-free IDE glucose sensor for continuous glucose monitoring throughout a day. FIG. 3F shows Clarke's error grid versus reference self-monitoring of blood glucose (SMBG) testing, suggesting the gel-free IDE sensor for fingertip perspiration as a reliable blood glucose sensing mechanism. Data points were collected from 5 healthy subjects consisting of 50 measurements operated before and 20 min after a meal over 5 days.

Figure 4A:
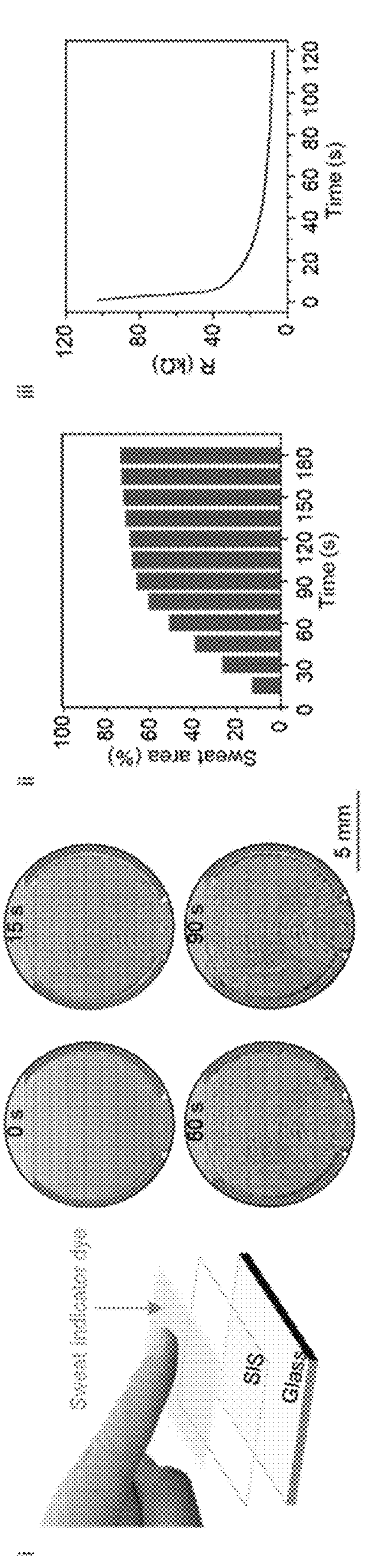
FIGS. 4A-4G shows designs and usage optimization of the solid state, gel-free touch-based IDE sensor.
Figure 4B:
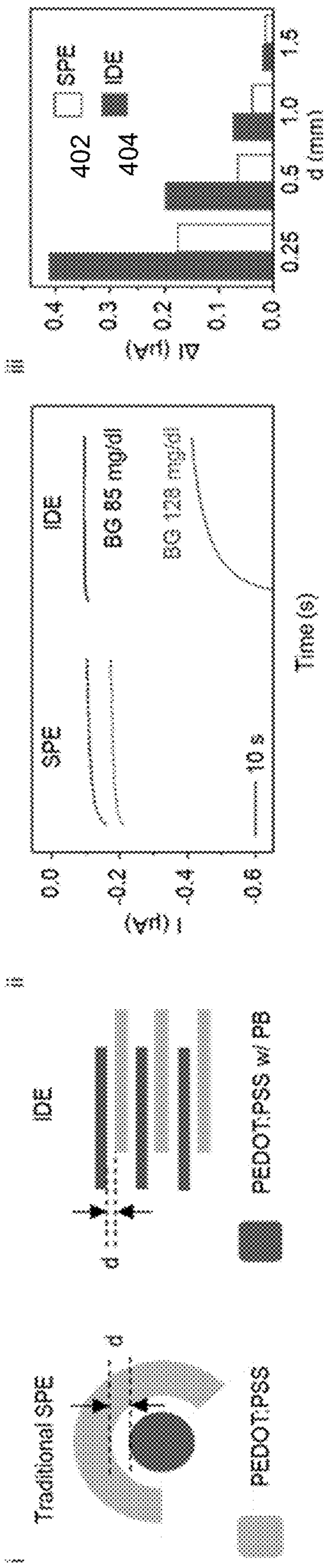
Figure 4C:
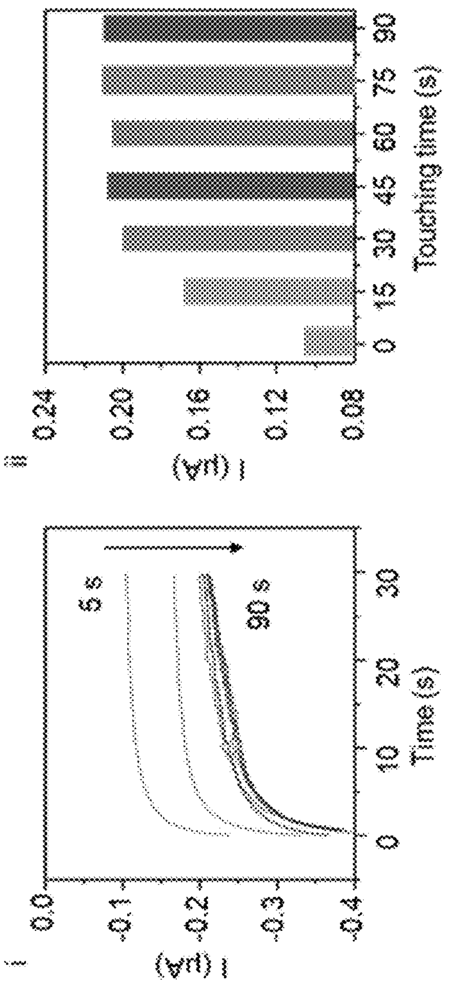
Figure 4D:
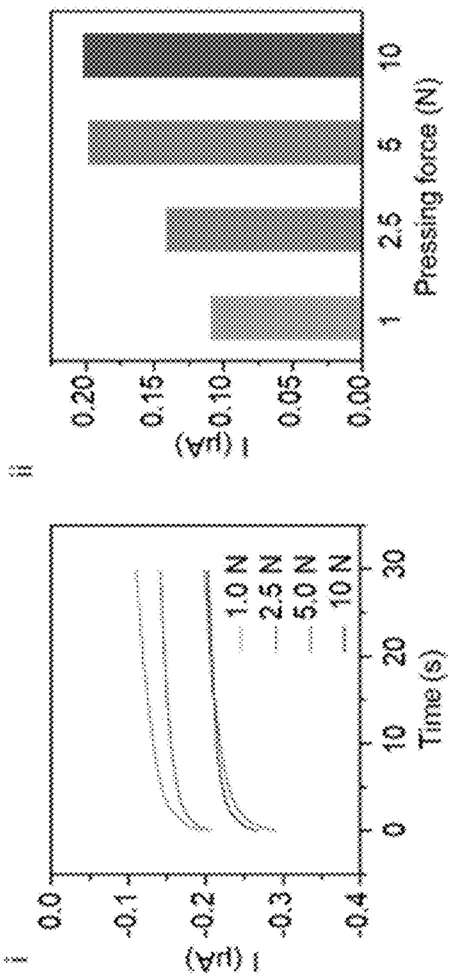
Figure 4E:
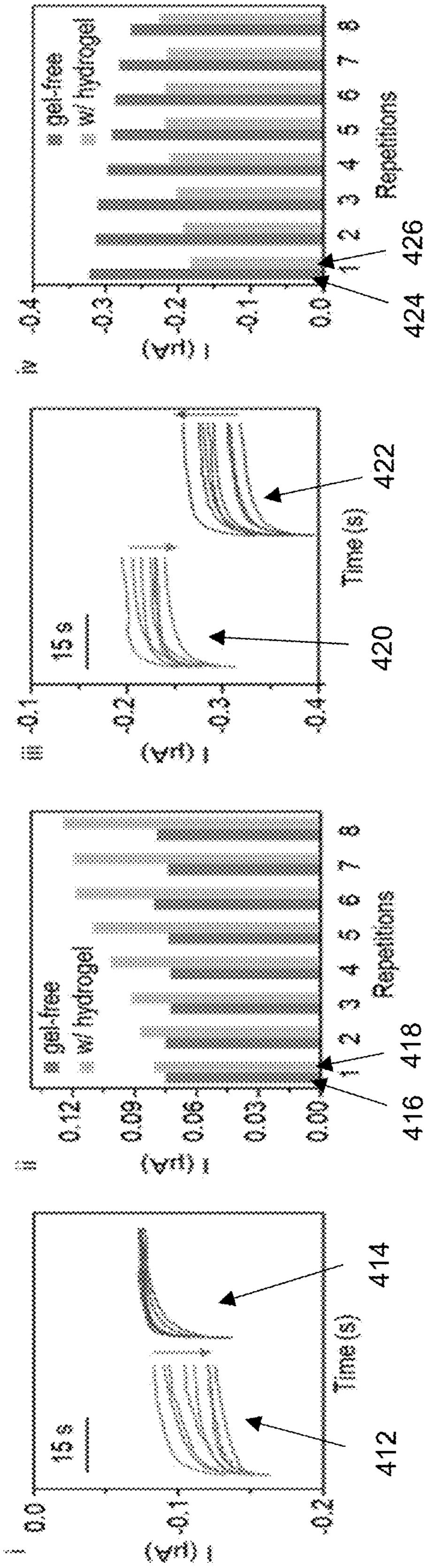
Figure 4F:
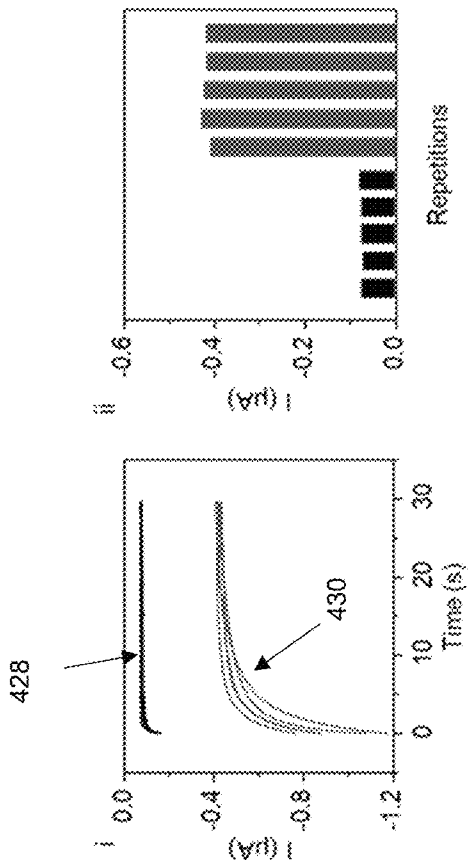
Figure 4G:
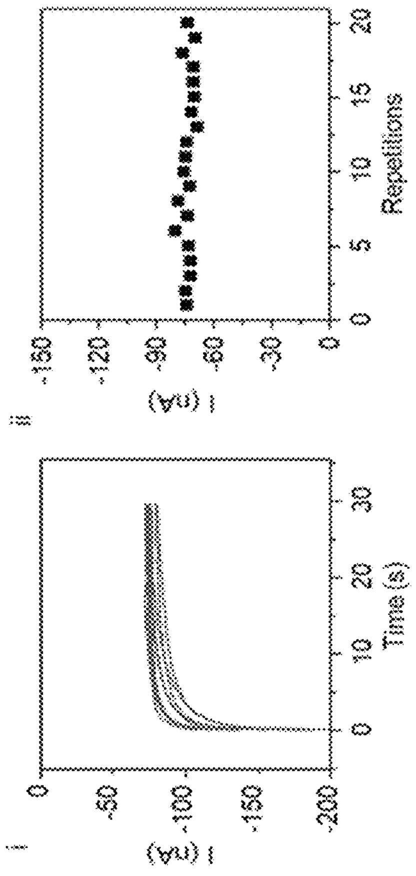

FIGS. 4A-4G shows designs and usage optimization of the gel-free touch-based IDE sensor. FIG. 4A is an illustration of (i) an experimental setup for visualizing the perspiration on the fingertip when pressed against the sensor and the corresponding optical images of the fingertip with indicator turning blue with sweat within the grooves, (ii) the corresponding area % covered by sweat indicated by color-changing dye, and (iii) the resistance between the anode and cathode vs. pressing time. FIG. 4B shows (i) schematics of traditional screen-printed electrode (SPE) and IDE design with controlled inter-electrode distance d, (ii) chronoamperometry (CA) response of the gel-free electrode in traditional SPE (left) and IDE (right) design with an inter-electrode spacing of 0.25 mm to finger perspiration, and (iii) summary of the change of the CA current response to finger perspiration with different inter-electrode distances, corresponding to capillary blood glucose levels of 85 mg/dl (402) and 128 mg/dl (404). FIG. 4C shows (i) CA curves and (ii) the final current signal after different touching (sweat accumulation) times as the finger pressed against the sensor. FIG. 4D shows (i) CA curves and (ii) the final current signal with different pressing pressures. FIG. 4E shows (i) CA response for a subject with steady glucose level with 6 repeated touches on the hydrogel-covered electrode (412), and the solid-state electrode (414) before a meal, (ii) the bar graph (416, 418) summarizing the current signals, and (iii) CA response for a subject with a falling glucose level after a meal with 6 repeated touches on the hydrogel-covered electrode (420) and solid-state electrode (422), and (iv) bar graph (424, 426) summarizing the current signals. FIG. 4F show reproducibility of the sensor with 5 repeated measurements at 3 min intervals: in FIG. 4F(i), line 428 indicates fingertip sensing corresponding to a capillary blood glucose (CBG) of 83 mg/dl before a meal, and line 430 indicates fingertip sensing corresponding to a CBG of 132 mg/dl after a meal; in FIG. 4F(ii), the corresponding bar graph demonstrates the reproducibility of the results before and after the meal, resulting in RSD of 2.4% and 1.9%, respectively. FIG. 4G shows (i) 20 repeated measurements performed in 3 min intervals (total 60 min) at a fasting blood glucose level, and (ii) reproducibility of these 20 repeated measurements; RSD 3.9%.

Figure 5A:
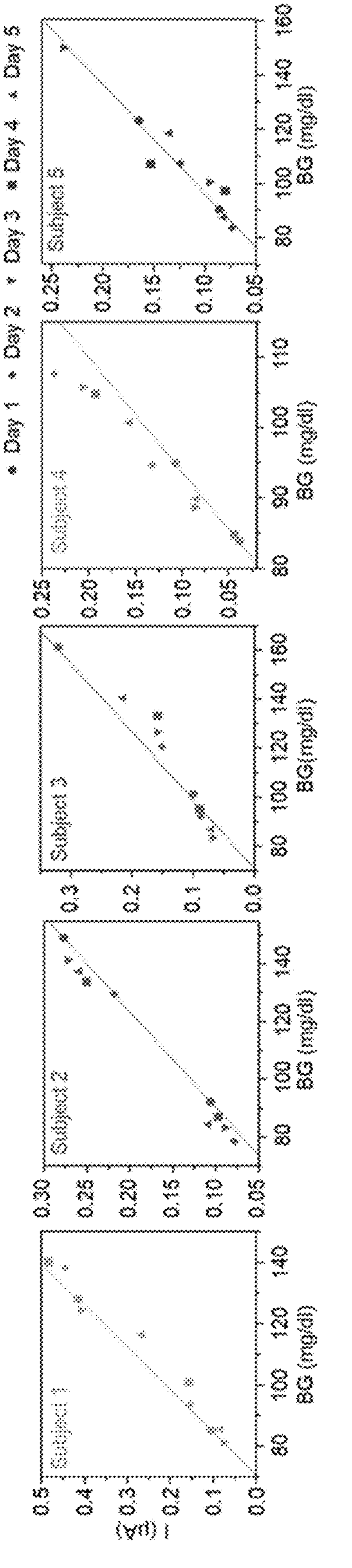
FIGS. 5A-5D show calibration and extended on-body evaluation of the solid state gel-free touch-based glucose sensor.
Figure 5B:
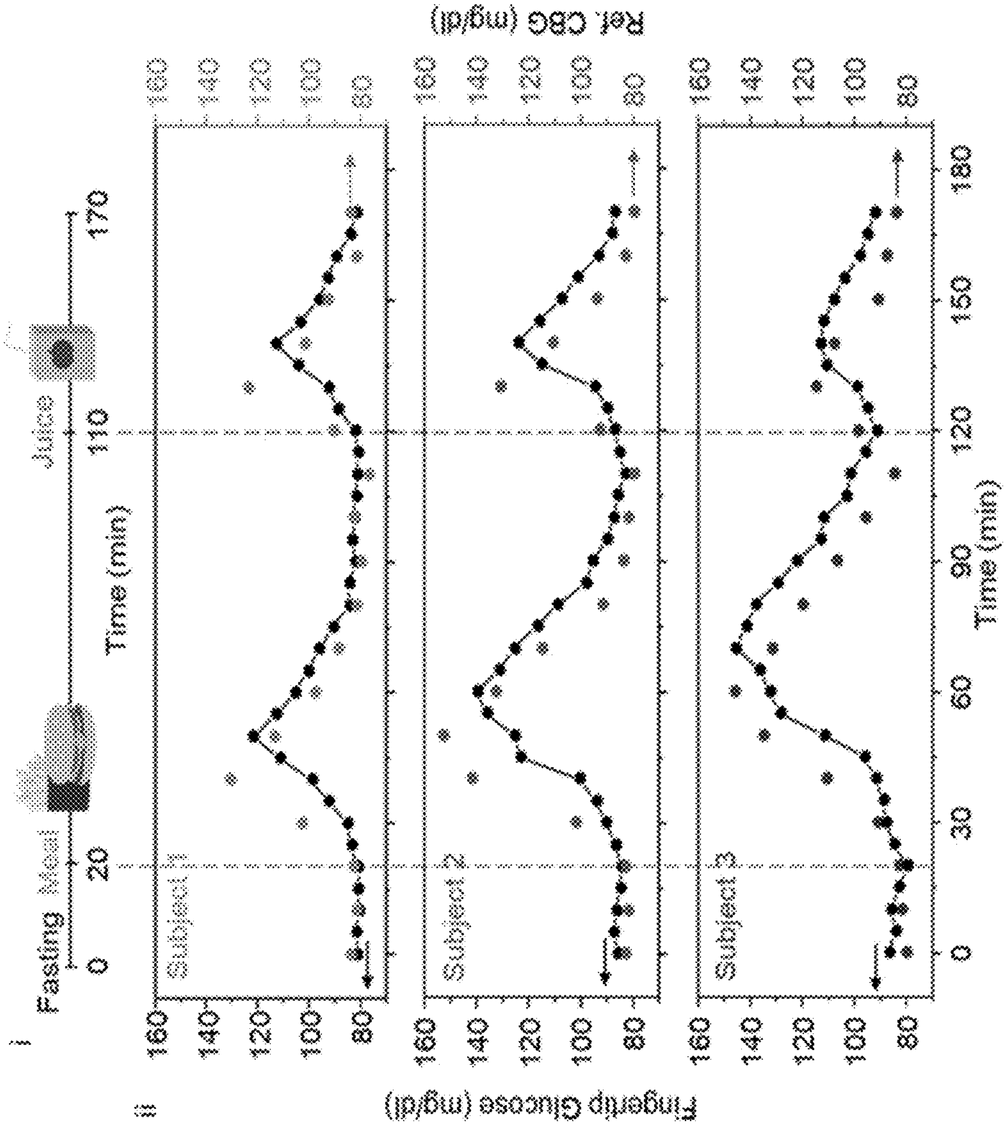
Figure 5C:
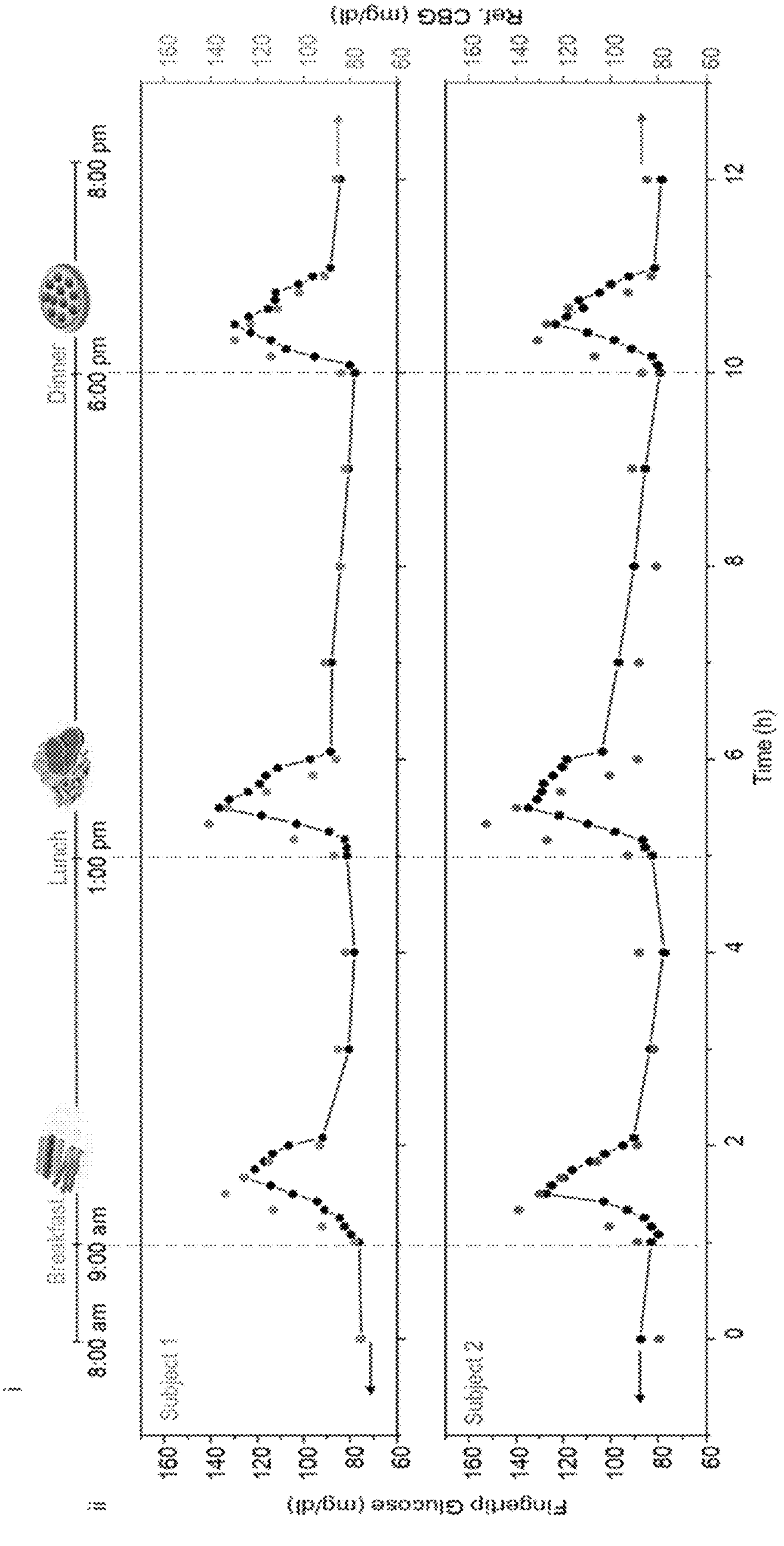
Figure 5D:
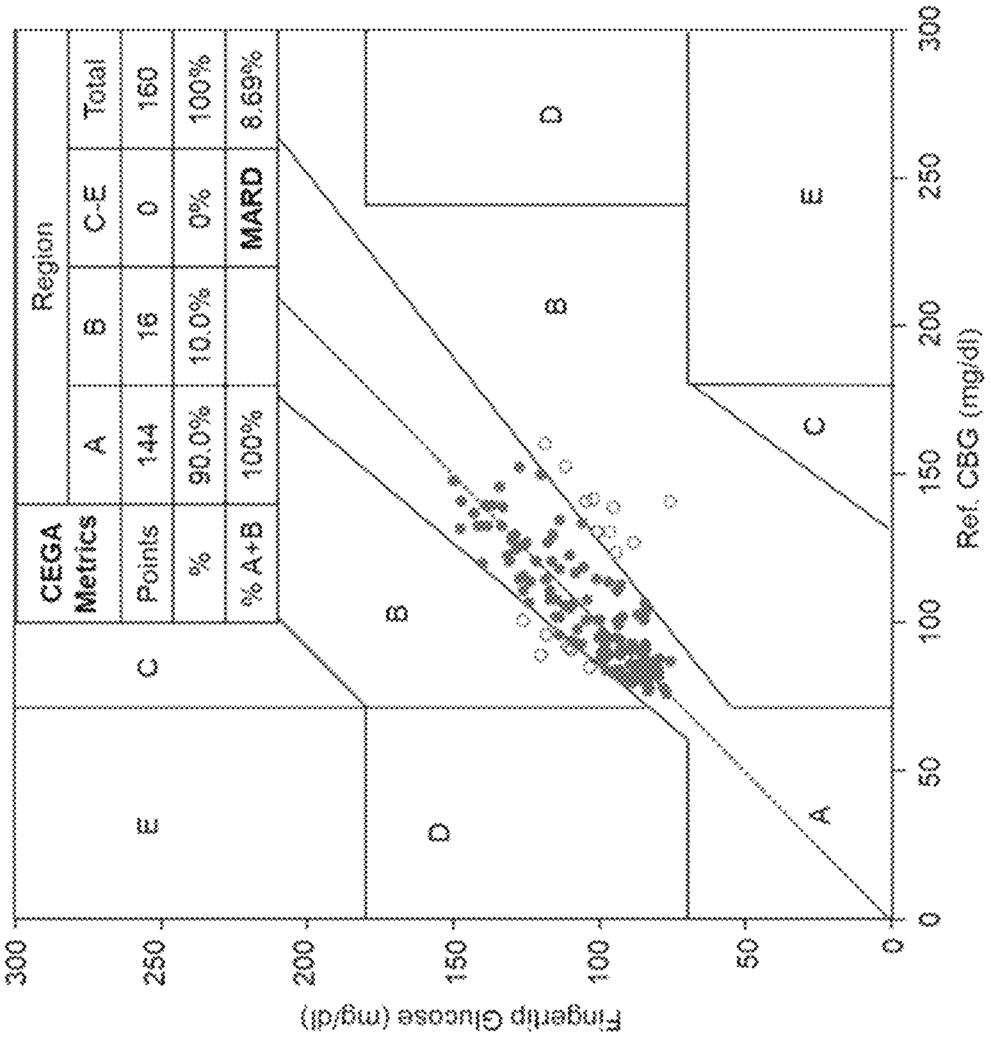

FIGS. 5A-5D show calibration and extended on-body evaluation of the gel-free touch-based glucose sensor. FIG. 5A shows the current response of the touch-based glucose sensor against the corresponding fingerstick SMGB reference and the corresponding linear regressions generated from 5 healthy subjects obtained before and after a meal in 5 subsequent days. Subjects include both males and females with ages between 22 and 36. FIG. 5B shows (i) schematic diagram representing the time course for the extended continuous glucose monitoring over 170 min, during which the same food and drink were provided to the volunteers after 20 and 110 min of test, while the touch-based glucose sensor and fingerstick SMBG signals were recorded every 5 and 10 min, respectively, and (ii) touch-based glucose sensor results of three non-diabetic volunteers converted using the $1^{st}$-day calibration along with their corresponding fingerstick SMBG. FIG. 5C shows schematic diagram representing the time course for the extended 12-hour glucose monitoring trial, during which high carbohydrate meals were provided to non-diabetic individuals 1, 5, and 10 h after starting the test: (i) touch-based glucose sensor and fingerstick SMGB signals were collected every 5 and 10 min, respectively, in the 1 h after the meal, and every 1 h between the meals; (ii) touch-based glucose sensor results of two non-diabetic volunteers were converted using the $1^{st}$-day calibration along with their corresponding fingerstick SMGB references. FIG. 5D shows Clarke error grid analysis of the touch-based glucose sensor versus the SMGB glucose as reference.

Figure 6:
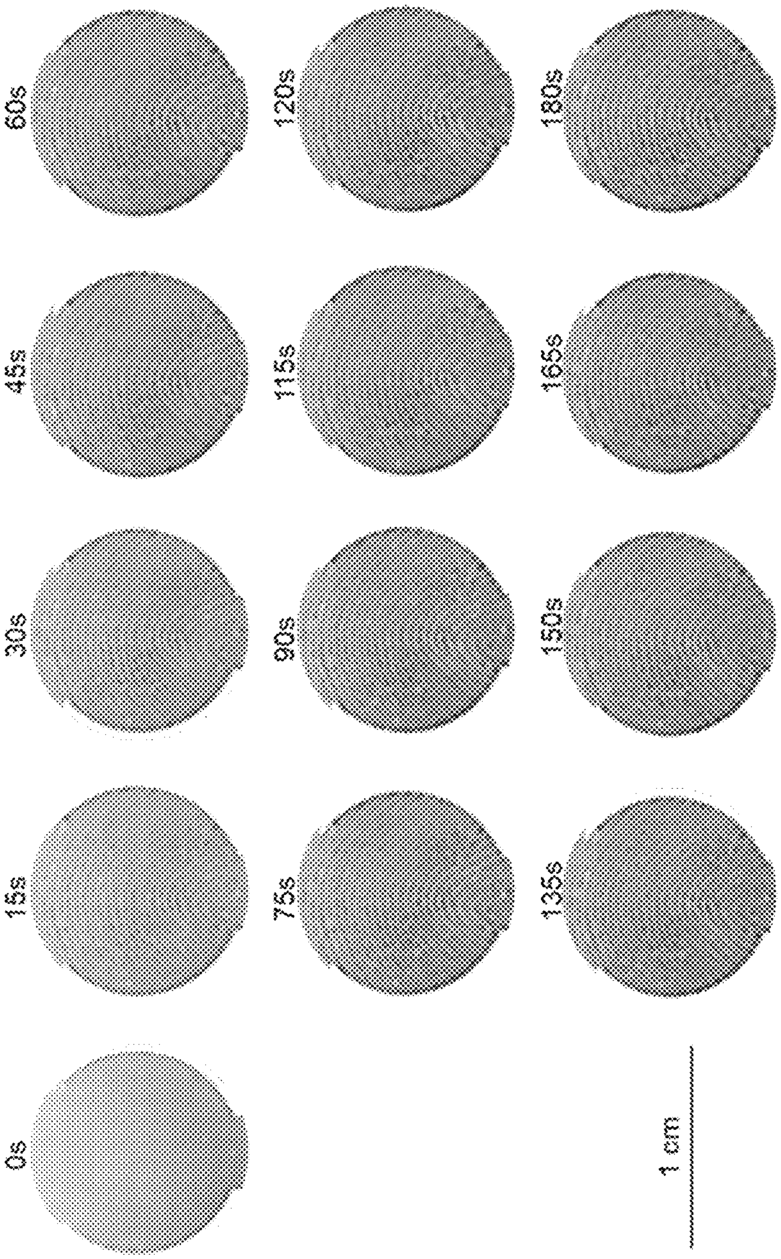
FIG. 6 shows dye experiment visualizing the distribution of sweat along the fingertip with the progression of time.

FIG. 6 shows dye experiment visualizing the distribution of sweat along the fingertip with the progression of time.

Figure 7A:
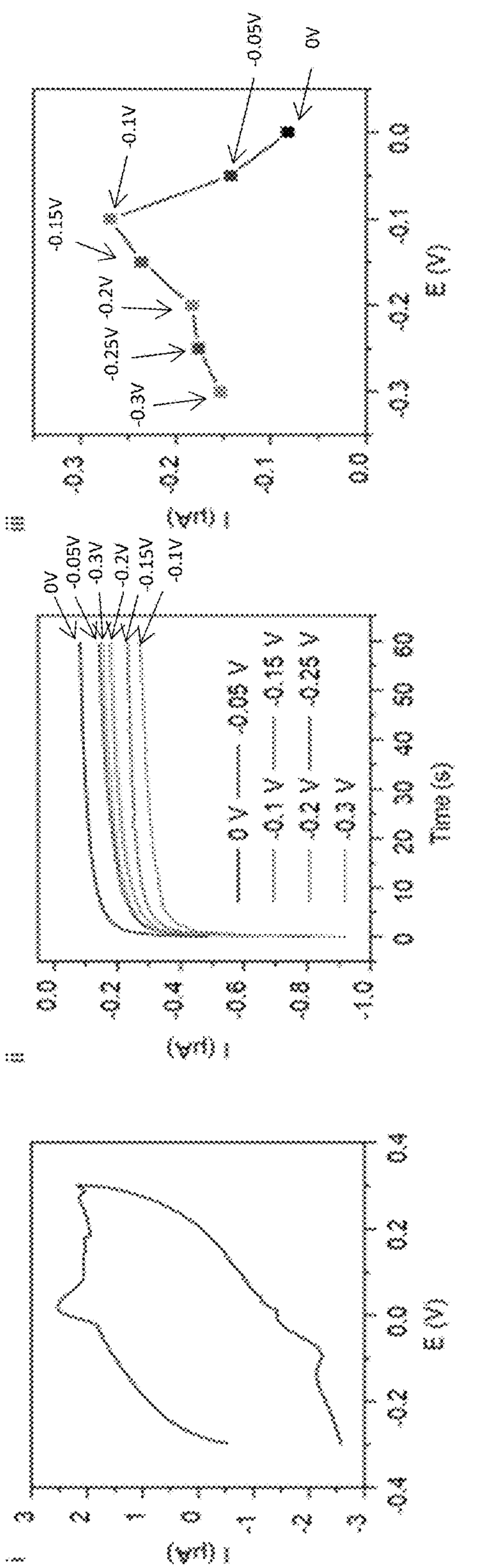
FIGS. 7A and 7B show in-vitro characterization of the IDE sensor.
Figure 7B:
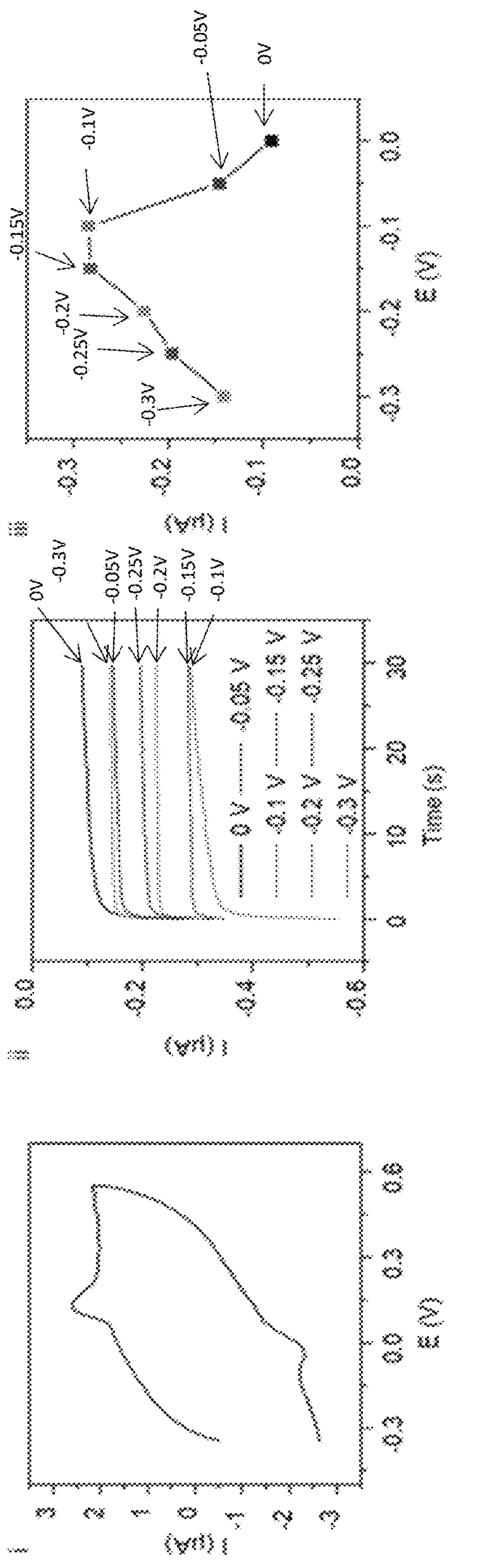

FIGS. 7A and 7B show in-vitro characterization of the IDE sensor. FIG. 7A shows (i) characterization of the IDE sensor in PBS (pH=7.3), including 2-electrode CV, (ii) CA at different potentials from 0 V to −0.3 V, and (iii) the current vs. potential plot, suggesting the optimal potential of −0.1 V (cathode vs. anode). FIG. 7B shows (i) characterization of the IDE sensor in artificial sweat (pH=7), including 2-electrode cyclic voltammetry, (ii) chronoamperometry at different potentials from 0 V to −0.3 V, and (iii) the current vs. potential plot suggesting the optimal potential of −0.1-−0.15 V (cathode vs. anode).

Figure 8A:
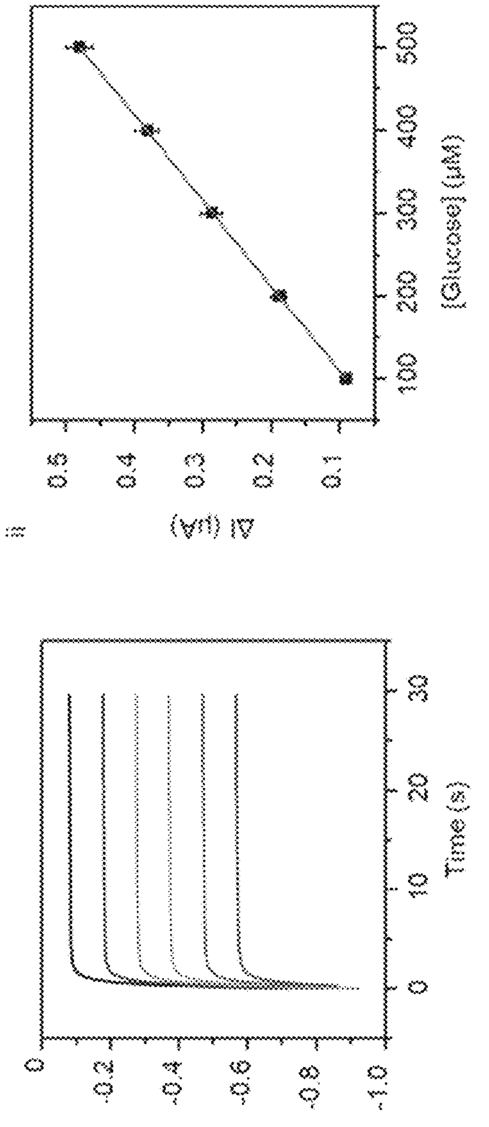
FIGS. 8A and 8B shows in-vitro calibration of the IDE glucose sensor.
Figure 8B:
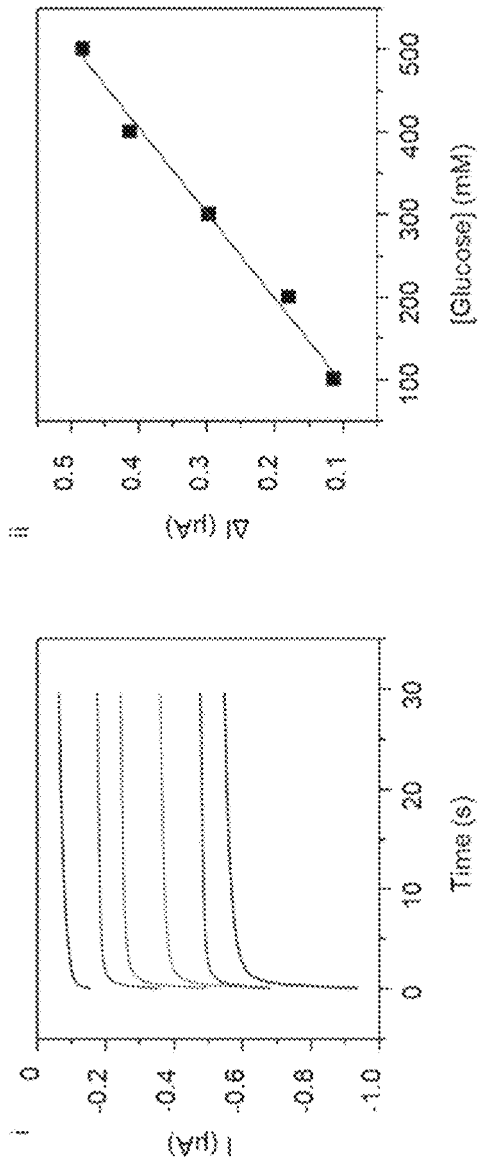

FIGS. 8A and 8B shows in-vitro calibration of the IDE glucose sensor. FIG. 8A shows (i) CA of the IDE with glucose concentrations of 100-500 μM in pH 7.3 PBS, and (ii) the resulting PBS calibration plot, with the sensitivity of 0.97 nA/μM (n=3, $r^2$=0.99). FIG. 8B shows (i) the CA of the IDE with glucose concentrations of 0-500 μM in pH 6.0 artificial sweat, and (ii) the resulting PBS calibration plot, with the sensitivity of 0.97 nA/μM.

Figure 9:
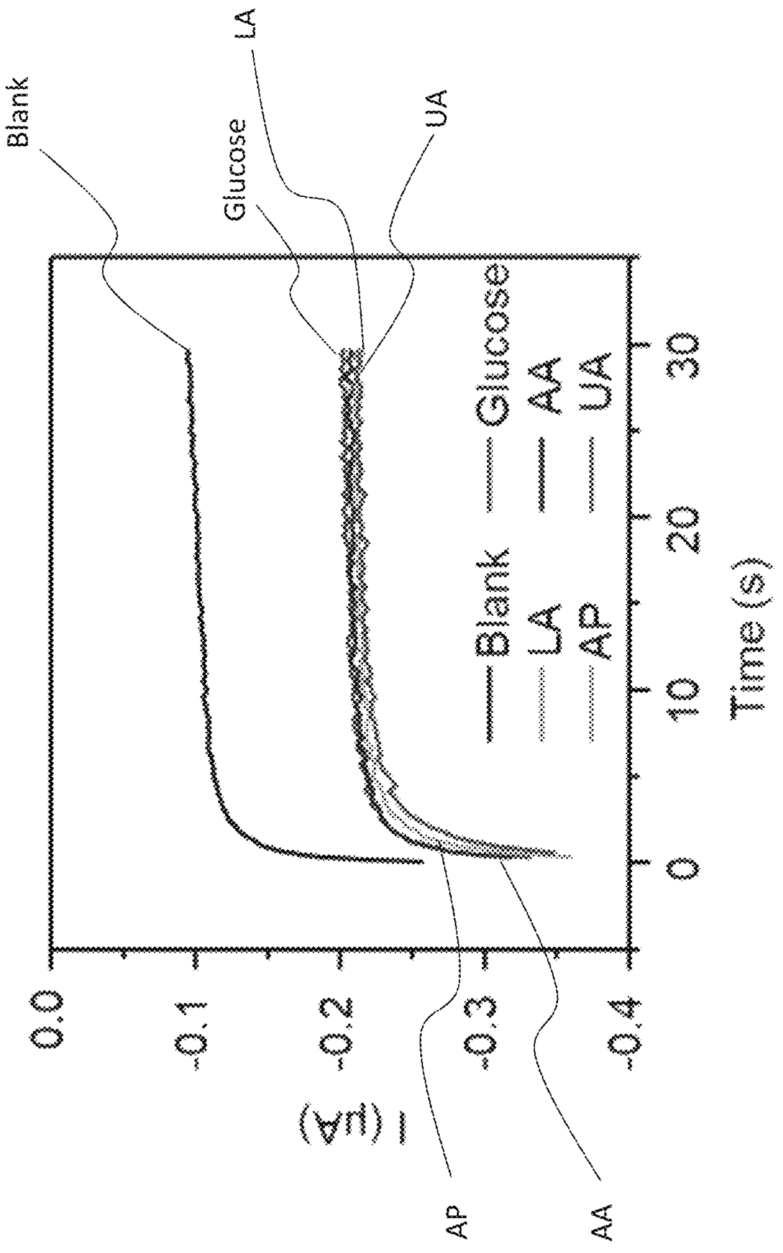
FIG. 9 shows selectivity of an IDE glucose sensor.

FIG. 9 shows selectivity of an IDE glucose sensor: CA response of the sensor in PBS (blank), and following additions of 100 μM glucose, lactic acid, ascorbic acid, acetaminophen, and uric acid, respectively.

Figure 10A:
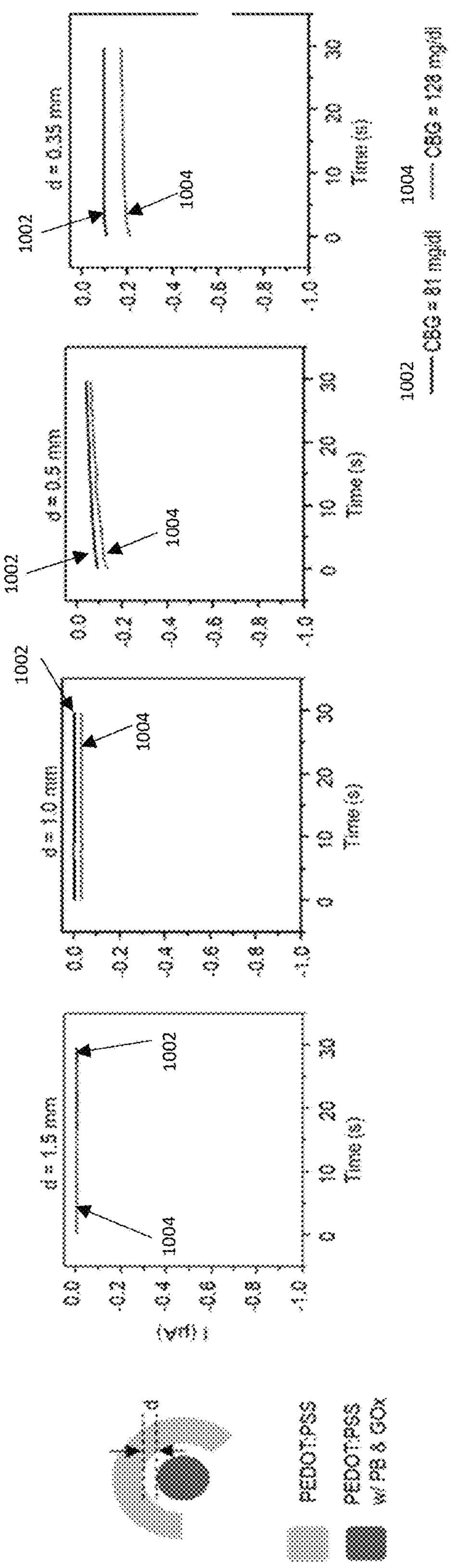
FIGS. 10A and 10B show optimization of the inter-electrode spacing.
Figure 10B:
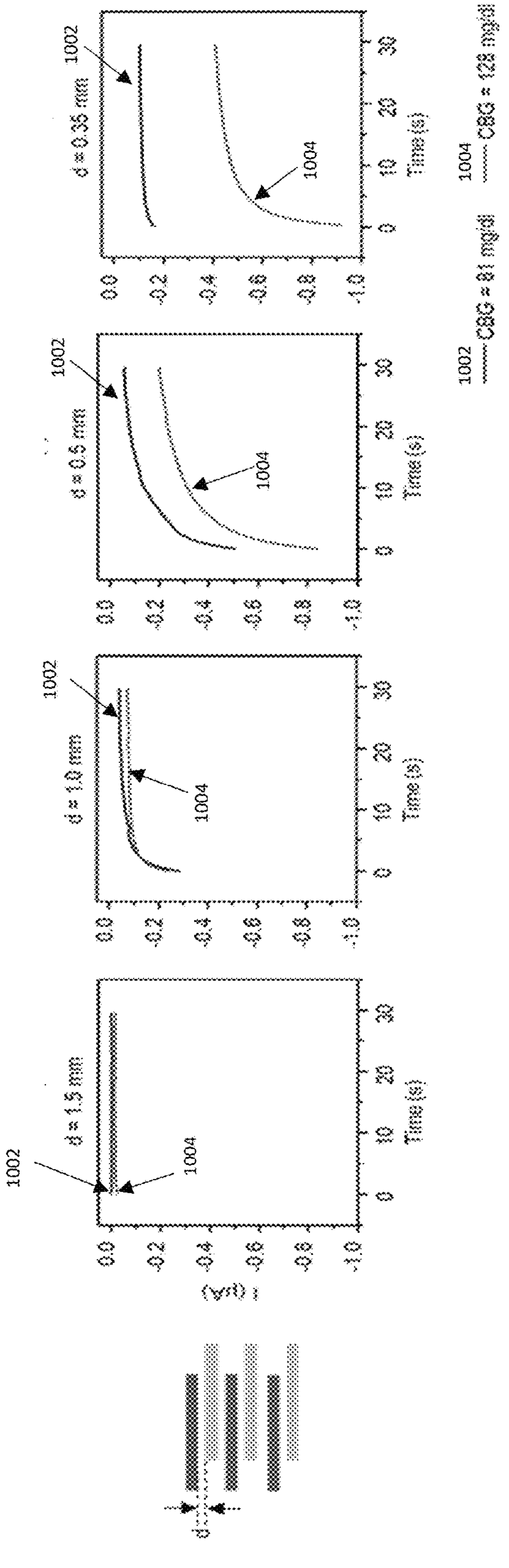

FIGS. 10A and 10B show optimization of the inter-electrode spacing. FIG. 10A shows CA response of typical SPE design with different electrode spacings. FIG. 10B shows CA response of the IDE design with different inter-electrode spacings.

Figure 11A:
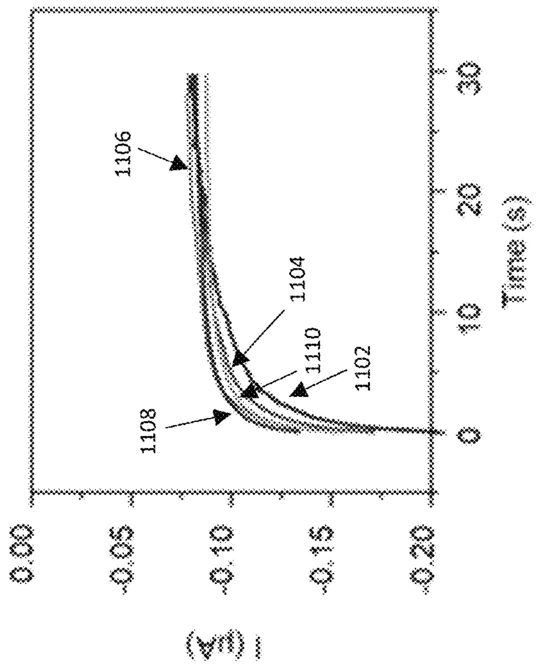
FIGS. 11A and 11B show sensor reproducibility characterization.
Figure 11B:
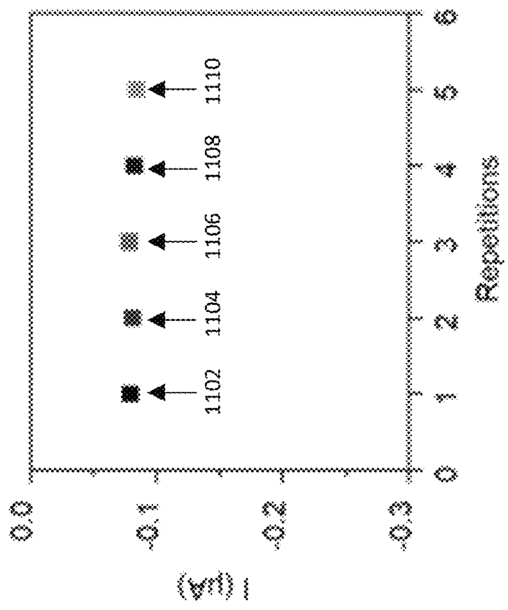

FIGS. 11A and 11B show sensor reproducibility characterization. FIG. 11A shows overlayed CA response of 5 different IDE glucose sensors, touched by the same subject with the same finger. FIG. 11B shows the corresponding results with an RSD of 4.3%.

Figure 12A:
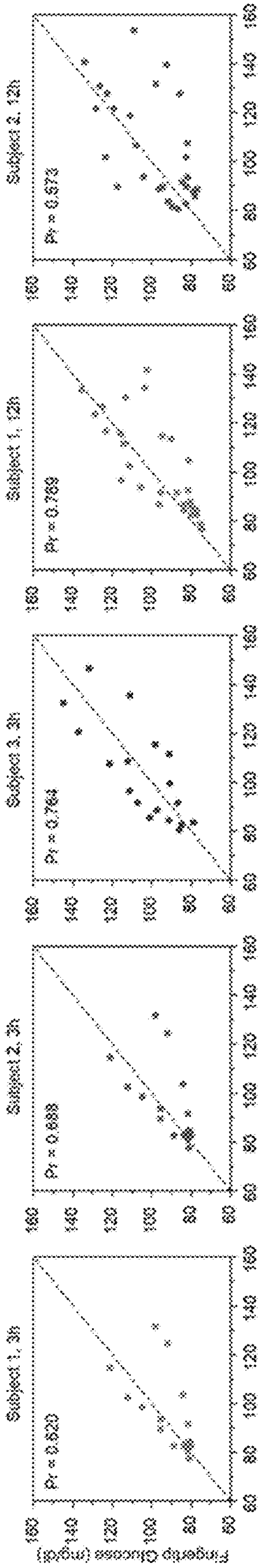
FIGS. 12A-12D show correlation of touch-based glucose level to fingerstick capillary blood glucose (CBG) in extended glucose monitoring trials of 3 and 12 h.
Figure 12B:
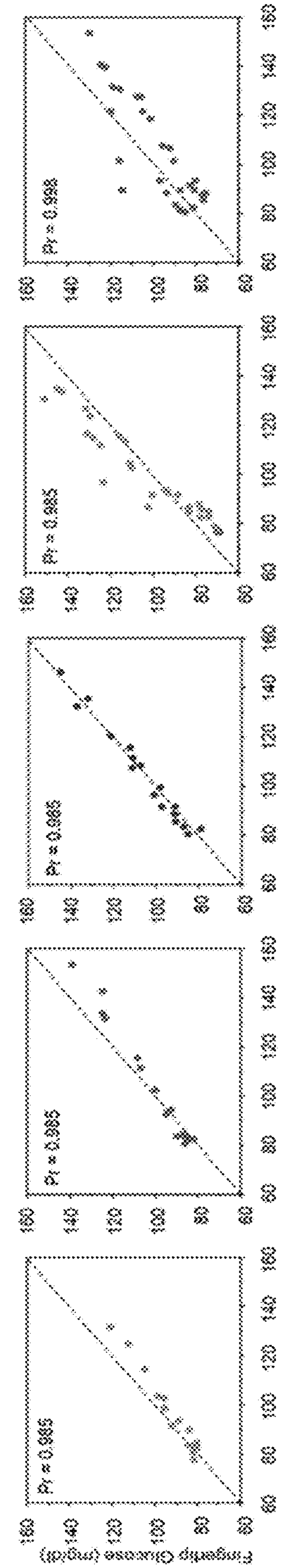
Figure 12C:
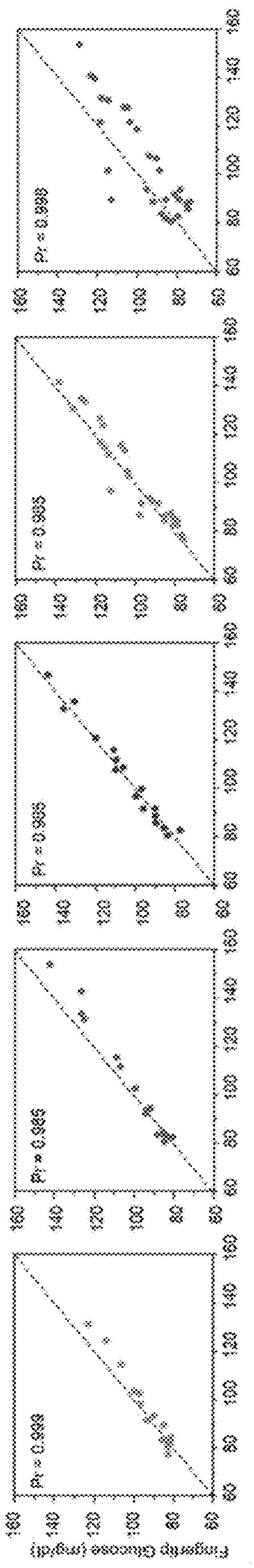
Figure 12D:
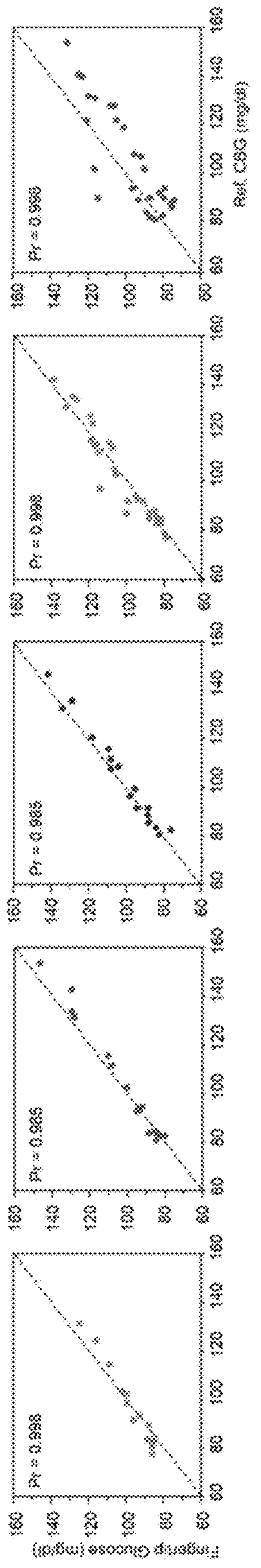

FIGS. 12A-12D show correlation of touch-based glucose level to fingerstick CBG in extended glucose monitoring trials of 3 and 12 h. FIG. 12A shows 1-day calibration without accounting for any time delay. FIG. 12B shows 1-day calibration with 10 min delay. FIG. 12C shows 3-day calibration with 10 min delay. FIG. 12D shows 5-day calibration with 10 min delay. The Pearson correlation coefficients are labeled in their corresponding subfigures.

Figure 13A:
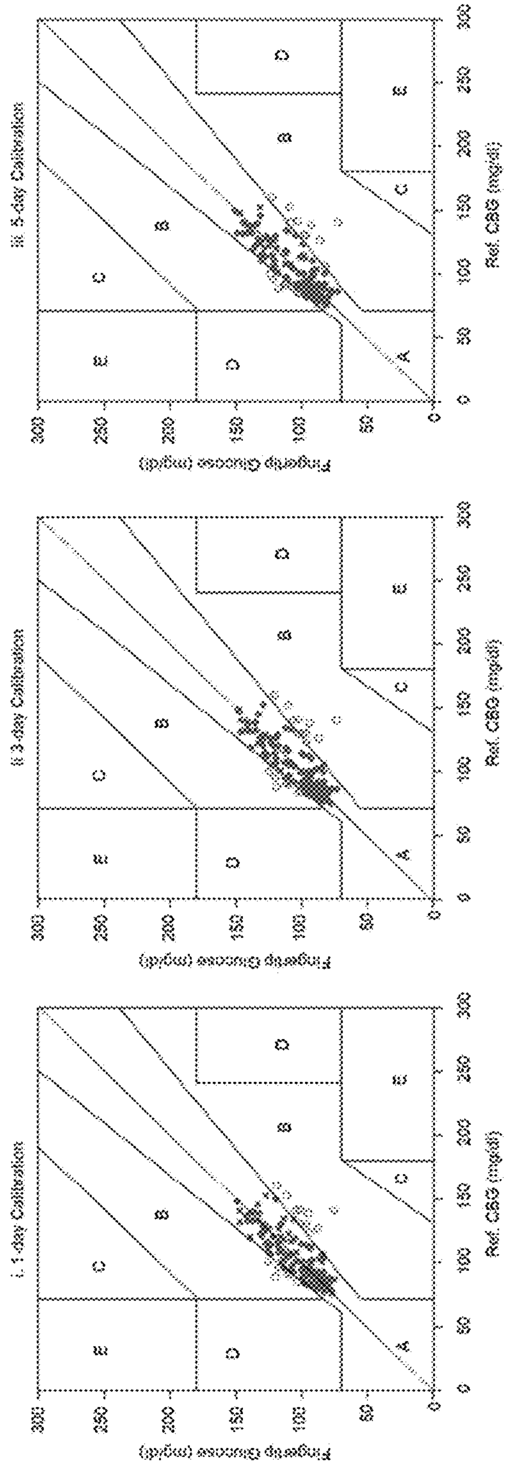
FIGS. 13A and 13B show Clarke's error grid analysis (CEGA) with additional calibration and time-delay corrections.
Figure 13B:
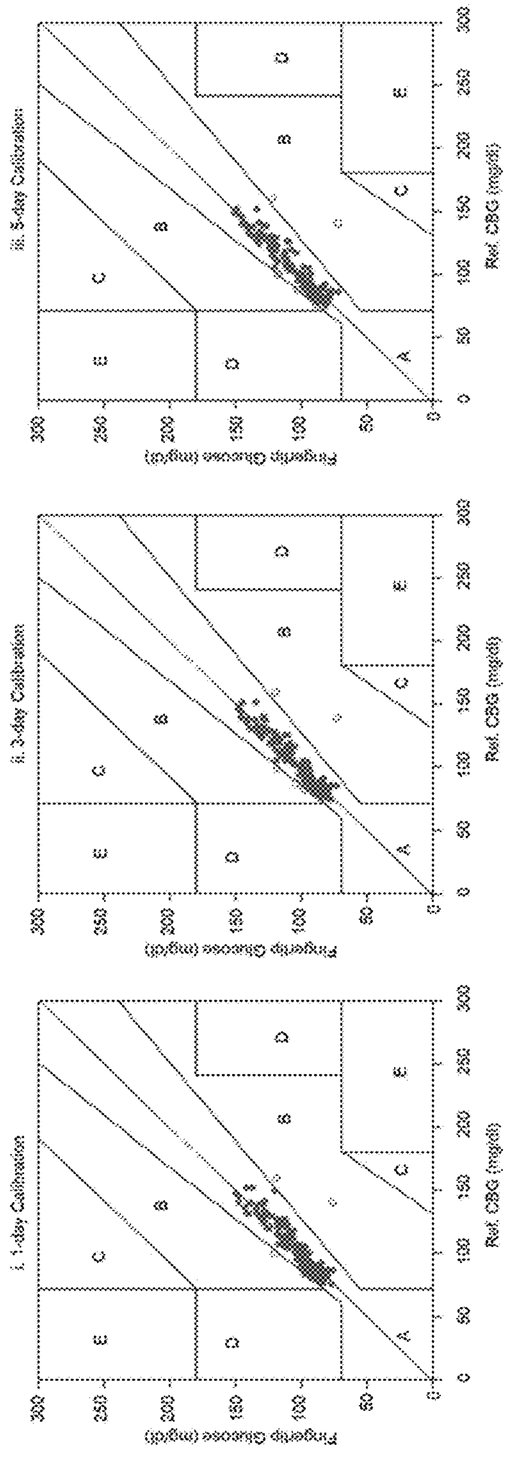

FIGS. 13A and 13B show CEGA with additional calibration and time-delay corrections. FIG. 13A shows the CEGA with (i) 1-day, (ii) 3-day, and (iii) 5-day calibrations, without accounting for any time delay. FIG. 13B shows CEGA with (i) 1-day, (ii) 3-day, and (iii) 5-day calibrations when accounting for the 10 min delay between CBG and the fingertip sweat glucose.

Type 1 diabetes is a chronic disease that requires frequent blood glucose testing for preventing acute and long-term complications. Common glucose monitoring methods, including finger-pricking capillary blood tests and subdermal continuous glucose monitors, are painful and invasive, respectively, whereas recent non-invasive epidermal sensors are limited in practicality and reliability. The disclosed technology can be implemented in some embodiments to provide a convenient, rapid, and accurate approach using interdigitated electrode transducer for frequent touch-based sweat glucose biosensing that leverages the passive perspiration from the fingertip. The interdigitated design establishes a solid-state interface and eliminates the need for sweat-collecting hydrogels, which greatly simplifies the sensing workflow and grants stability and reusability. The sensor can be used repeatedly for day-long glucose self-monitoring and delivers reliable glucose data with the low mean-absolute relative difference of 8.69%, comparable to that of commercial fingerstick and continuous glucose monitors. The new protocol based on some embodiments provides convenient, practical, and pain-free glucose sensing, promoting frequent self-testing and improved diabetic self-care.

Diabetes is a global health concern, ranking among the leading causes of death. Frequent monitoring of blood glucose levels is critical for understanding the disease progression and optimizing its control. While diabetes patients have relied over the past 3 decades on performing finger-pricking self-monitoring of blood glucose (SMBG) multiple times daily, the painful, inconvenient, and invasive nature of such finger-pricking step compromises patient compliance and greatly decreases the testing frequency. Continuous glucose monitoring (CGM) addresses these limitations of SMBG and offers significant improvements in the management of diabetes. While removing the need for finger pricking and providing more insights from continuous data, CGMs still use invasive (e.g., ~10 mm long) costly needles, require daily SMBG calibration, and are challenged by biofouling, long stabilization time, glucose time delay, and limited lifetime. While alternatives, such as non-invasive sweat and interstitial fluid (ISF) glucose sensors, have been proposed recently, their practicality is largely impeded by complex biofluid extraction mechanisms (e.g., exercise, sweat-inducing drug, reverse iontophoresis), which may induce unnatural metabolic activities or dilutions that affect the correlation with blood glucose concentrations. Indeed, it was demonstrated that sweat glucose can accurately reflect blood glucose levels upon proper harvesting of sweat. Recent advances cleverly leveraged the direct sampling of the passive, thermoregulatory sweat from the high-sweat-rate fingertip for chemical sensing, leading to the monitoring of cortisol, levodopa, glucose, caffeine, lactate, and ascorbic acid concentrations. However, such touch-based sensing has relied on hydrogel as a sweat collection interface (made of agarose or polyvinyl alcohol), mounted on the sensor, which leads to major challenges and errors due to analyte carry-over, dilution, and solvent evaporation. The use of the hydrogel interface thus suffers from inconsistent sensing results and requires inconvenient lengthy gel replacement, hence greatly impeding the reliability, repeatability, durability, simplicity, and overall practicality of such technology.

The disclosed technology can be implemented to address the above issues by providing a reusable solid-state touch-based electrochemical sensing protocol for reliable, frequent extended glucose monitoring. To eliminate the need for hydrogels, the sensor relies on a solid-state interdigitated electrode (IDE) design, which consists of a poly(3,4-ethylene dioxythiophene) polystyrene sulfonate (PEDOT:PSS) anode and PEDOT:PSS-Prussian blue (PB) cathode, printed on a styrene-isoprene-styrene block copolymer (SIS) substrate. These printed IDE electrodes are decorated with the glucose oxidase (GOx) enzyme that reacts selectively with the glucose in the fingertip sweat for subsequent detection (FIG. 3A). The interdigitated PEDOT:PSS electrode design endows the ability for direct touch-based measurement of sweat glucose without any hydrogel or ionically conductive interface, with the passive perspiration spreading rapidly along the grooves of the fingertip, establishing ionic pathways between the anode and cathode of the IDE (FIG. 3B). Using the conductive PEDOT:PSS polymer endows ion transport and low electrode impedance, which are favorable towards solid-state bioelectronic interfaces. Relying on the fast natural perspiration on the fingertip, the solid-state IDE biosensor can provide accurate non-invasive sweat sensing within 90 s, including 60 s of sweat accumulation followed by 30 s of chronoamperometry (CA) at the low voltage of −0.1 V to offer a highly selective current response that can be readily calibrated to blood glucose. Such simple, rapid user-friendly pain-free glucose self-testing provides high sensing frequency, comparable to state-of-art CGM technology (1 data point per 1.5-15 min), yet in a completely non-invasive manner. This protocol thus allows users to closely track their blood glucose level and capture dynamic events involving rapidly fluctuating concentrations (FIG. 3C). Furthermore, eliminating the hydrogels and related chemical buildup, allows reusing the same sensor throughout the day (after a quick gentle wipe with a tissue), and obviates the need for any stabilization time. The sensor generates a highly reproducible signal upon repeated use and is highly reversible to follow sharp fluctuations of blood glucose concentrations (FIG. 3D). A single sensor strip can be used reliably for day-long continuous glucose testing to allow the users to track their glucose level and detect potential glycemic abnormalities conveniently and closely (FIG. 3E). An initial first-day, simple 2-data-point personalized calibration (at different blood glucose levels) is used fully address inter-person variations (e.g., sweat rate). The sensor delivers highly accurate blood glucose concentration data, closely matching the capillary blood glucose (CBG) level of commercial fingerstick with short time delay and features low mean absolute relative difference (MARD) of 8.69% and with 89.4% zone-A ratio in Clarke's error grid analysis (CEGA) (FIG. 3F), comparable to the accuracy of commercial CGM and fingerstick SMBG.

To fully utilize the low volume of sweat on the fingertip, the sweat distribution on the surface of the fingertip was examined closely by using the color-changing bromocresol green dye that turns blue upon contact with the sweat. As shown in FIG. 4A i, an SIS substrate uniformly coated with a thin layer of the dye was placed on a glass slide, and a video was taken, recording the color change of the dye upon pressing a clean, dry finger against the substrate (FIG. 6,). As time progressed, most of the grooves are covered by sweat within 60 s, establishing a conduction pathway between the anode and cathode (FIG. 4A ii). While the color of the dye darkens with time, no additional area is covered by sweat. This agrees with measurements of the internal resistance between the two electrodes, which has mostly stabilized after 60 s (FIG. 4A iii).

The performance of the gel-free touch-based sensor for glucose monitoring was characterized first in-vitro using glucose in phosphate buffer solutions (PBS) at pH 7. The optimal potential was optimized at −0.1V between cathode and anode, which results in the highest CA response. Similarly, the sensor was evaluated in artificial sweat (with a lower pH of 6), showing that the optimal potential and response are unaffected by the lower pH (FIGS. 7A, 7B, 8A and 8B). The advantage of the solid-state IDE electrode was then tested with a human subject's fingertip in comparison to the traditional screen-printed electrode (SPE) sensor design along with the hydrogel sweat collection interface. Compared to the SPE disk design, the IDE layout reduces the inter-electrode spacing while maximizing the number of electrical connections between the anode and cathodes (FIG. 4B i). As a result, when sensing from the same finger, the sensitivity of the IDE is considerably higher than the SPE, even with a similar inter-electrode distance (FIG. 4B ii). In general, the sensitivity increases upon decreasing the inter-electrode spacing down to 0.25 mm, which was used in subsequent measurements (FIG. 4B iii, FIGS. 10A and 10B). Different sweat accumulation times prior to the CA measurements were evaluated, showing that the response increases gradually with the touching time up to 45 s and then it starts to level off (FIG. 4C), which agrees with the results of FIG. 4A. The pressing force against the electrode was also optimized; the results (shown in FIG. 4D) indicate that 5 N per finger is sufficient to reach a stable signal.

The IDE design thus allows the solid-state contact-based fingertip sensing, offering significant advantages over common hydrogel-based sweat collection mechanisms in terms of simplicity, reusability, testing frequency, and data reproducibility. As a comparison, the same finger was tested repeatedly on the same sensor with and without the hydrogel with steady and falling glucose levels (before and 30 min after a meal, respectively). As shown in FIG. 4E i-ii, in the case of constant glucose level, the hydrogel-covered sensor displays an increasing current signal due to the carry-over and build-up of glucose from repeated touches, while the solid-state IDE sensor shows good stability, with negligible difference through these repeated touches. In contrast, in the case of a falling glucose level (FIG. 4E iii-iv), the solid-state IDE sensor can accurately capture the dynamically decreasing glucose concentrations, whereas the hydrogel-covered sensor shows a slowly increasing response due to the combination of competing effects of the decreasing glucose concentration and its buildup in the gel, leading to unrealistically increasing response associated with such carry-over effects. The reproducibility of the sensor at different glucose concentrations was investigated from five repeated tests at the fasting state (CBG=83 mg/dl) as well as 20 min after a meal (CBG=132 mg/dl)(FIG. 4F). Highly reproducible CA signals are observed for these repetitive touch-based measurements, leading to RSD values of 2.4% and 1.9%, respectively. Furthermore, the repeatability of the glucose sensor was evaluated over an extended period of 60 min, involving 20 repeated tests at 3 min intervals at a fasting blood glucose level (FIG. 4G). The highly reproducible current signals over this long series, with a low RSD value of 3.9% (n=20), reveal the good repeatability for multiple repeated frequent measurements. In addition, characterization of the sensor's selectivity and reproducibility were carried out (FIGS. 9, 11A and 11B).

Following the systematic optimization and characterization, the accuracy of the touch sensor was assessed with five healthy, non-diabetic male and female subjects between the ages of 22-36. Due to the individual differences (e.g., sweat rate, fingertip size), each subject was tested initially before and 20 min after meals to construct a personalized calibration between the CA signal of the gel-free touch-based glucose sensor and the CBG level obtained from fingerstick SMBG (FIG. 5A). Throughout the 10 data points generated over the initial 5 days, five subjects have obtained the calibration with Pearson's values above of 0.98, 0.99, 0.96, 0.96, and 0.99, respectively, suggesting a consistent correlation between the glucose in passive perspiration from the fingertip and the fingertip blood level throughout different days. Such consistency obviates the need for repeated re-calibrations; only the 1$^{st}$-day data points were thus used for subsequent personal calibration.

TABLE 1

The statistics of the sensor using different calibration methods

| | No delay | | | 10 min delay | | |
|---|---|---|---|---|---|---|
| | 1-day calibration | 3-day calibration | 5-day calibration | 1-day calibration | 3-day calibration | 5-day calibration |
| MARD | 8.69% | 8.27% | 8.46% | 5.37% | 4.79% | 4.76% |
| CEGA Zone A | 89.4% | 87.5% | 88.1% | 98.0% | 96.7% | 96.7% |
| CEGA Zone B | 10.6% | 12.5% | 11.9% | 2.0% | 3.3% | 3.3% |

The ability to use the touch-based gel-free glucose sensor for replacing fingerstick SMBG toward frequent non-invasive and rapid glucose sensing was evaluated first over a 3 h period, during which all subjects consumed a high-calorie meal followed by a sugar-rich juice, while performing the touch-based sensing (with the same sensor) every 5 min and fingerstick CBG reference measurements at 10 min intervals (FIG. 5B i). As shown in FIG. 5B ii, the glucose levels (estimated from the 1's day calibration) have shown good agreement with the reference CBG concentrations for all three subjects. Further exploring the solid-state IDE glucose sensor as a potential alternative to the CGMs, an extended day-long glucose monitoring was performed over the period of 12 h. During this time, subjects have taken breakfast, lunch, and dinner; in parallel, the touch sensing and fingerstick CBG measurements were carried out every 5 min and 10 min, respectively, within the hour after the meal, in addition to hourly measurements between the meals (FIG. 5C i). The results from two subjects demonstrate continuous dynamic profiles of the glucose concentration over the entire day, with the high values and temporal trends in agreement between both methods of measurement (FIG. 5C ii). Notably, a ~10 min lag between the fingertip glucose level and the CBG is observed among all subjects in both the 3 h and 12 h trials, in agreement with earlier reports and reflecting the diffusive transport of glucose from capillary blood vessels to apocrine sweat glands. Similar time delays are observed in commercial CGM devices and are commonly addressed via various prediction algorithms that improve accuracy. By accounting for the 10-min time lags, the touch-based glucose calibration can be adjusted, further improving the correlations of the 5 trials, as shown in FIGS. 12A-12D, 13A and 13B and Table 1.

The mean absolute relative difference (MARD) and the Clarke's error grid analysis (CEGA) are common methods to evaluate the accuracy and reliability of the glucose-sensing technologies. Commercial CGM systems commonly feature MARD values between 9-14%. The gel-free touch-based sensor is characterized with a MARD of 8.69% (with data size n=160), which reflects its high accuracy, comparable to that of commercial glucose monitoring devices. With additional calibrations (vs blood; over initial 3-5 days, instead of the first one) has shown no significant improvement in MARD, whereas when accounting for the time delay, the MARD of the sensor can be further reduced to 4.76% (Table 1). The CEGA assesses the reliability of the glucose monitoring technology, by separating the grid into separate zones, A through E, with zone A corresponding to the values within 20% of the reference and means no effect on clinical action. As shown in FIG. 5D, the solid-state gel-free touch-based glucose sensor has 87.9% of data points landing in region A, with 100% of all values falling in the combined A plus B region, indicating high accuracy with very low chances of misdiagnosis of hypoglycemia and hyperglycemia. Notably, accounting for the 10 min time delay leads to even higher sensor reliability, with 98% of data in region A, whereas additional calibration data points did not significantly improve the accuracy (FIGS. 13A and 13B).

The disclosed technology can be implemented in some embodiments to provide a highly accurate, simple, and rapid glucose-sensing protocol using an interdigitated, solid-state PEDOT:PSS-based electrode, which leverages the passive perspiration of the fingertips to enable reliable near real-time non-invasive monitoring of glucose levels. Eliminating the need for the sweat collecting hydrogel interface greatly simplified the operation to allow frequent repetitive measurements over the entire day while offering superior analytical performance compared to traditional hydrogel-based SPE sensors. Compatible with diverse subjects, the sensor can rapidly establish personalized calibration (from merely initial 2 fingerstick measurements), showing considerable promise towards substituting painful, frequent finger pricking SMBG and invasive CGM technologies for extended day-long continuous glucose monitoring. The new protocol offers high accuracy with low MARD and good CEGA metrics, which are comparable to those of commercial glucose sensing technologies, along with painless (blood- and needle-free), rapid operation. The same low-cost sensor can be used without any re-stabilization, performing over 50 measurements throughout the day. Such convenient touch-based sensing greatly increases the frequency of self-testing compared to traditional SMBG, to offer enhanced diabetes control. The disclosed technology may also be implemented in some embodiments to enable large-scale validation using diverse subjects, and to increase further the speed and simplicity develop an advanced blood-free calibration process and prediction algorithm, along with improved understanding of the fingertip passive perspiration phenomenon and of the role of the electrode geometry at the hydrogel-free IDE setup. Translating such contact-based sensing into wearable devices towards passive, continuous monitoring of glucose day and night would further promote its practical usage as a true CGM alternative. Combined with engineering efforts for creating a user-friendly sensor prototype, these developments may lead to highly reliable pain-free rapid, and frequent self-testing of glucose for home and other decentralized settings towards improved management of diabetes, as well as for simplified and accurate non-invasive monitoring of other key sweat biomarkers.

In some implementations, graphite, toluene, acetone, ethanol, glutaraldehyde, D-(+)-glucose, glucose oxidase (GOx), Ag flake, potassium chloride (KCl), sodium chloride (NaCl), sodium phosphate anhydrous, Prussian blue, and sodium dodecylbenzene sulfonate (DBSS) may be used for fabrication of the interdigitated electrode based on some embodiments of the disclosed technology. In some implementations, Styrene-ethylene-butylene-styrene (e.g., SEBS G1645) triblock copolymer may be used for fabrication of the interdigitated electrode based on some embodiments of the disclosed technology. In some implementations, the screen printable PEDOT:PSS paste may be used for fabrication of the interdigitated electrode based on some embodiments of the disclosed technology.

Fabrication of the Interdigitated Electrode

In some implementations, the IDE sensor may be fabricated using layer-by-layer screen-printing with customized four kinds of inks: the electrochromic poly(3,4-ethylenedioxythiophene) polystyrene sulfonate (PEDOT:PSS) ink, the silver ink for interconnection, and an insulating resin composed of SEBS. The PEDOT:PSS ink may be formed using a mixture of ink prepared using 1 g of PEDOT:PSS paste, 0.2 mL of toluene, 0.15 mL DBSS (75 mg/ml in DI water), and 0.0135 mL of fluorosurfactant FS-65. To make the PEDOT:PSS-PB ink, similar components may be used, with additional 20 mg of PB powder that is added per 1 g of mixture. The stretchable silver ink may be synthesized. In some implementations, silver flakes, toluene, and SEBS may be mixed in a weight ratio of 4:2.37:0.63. All the inks may be homogenized by mixing them in a dual asymmetric centrifugal mixer, e.g., with a speed of 1900 RPM for 5 min. The insulating resin is prepared by dissolving SEBS a toluene solution (4:10 weight ratio). The solution is then mixed at 1900 RPM for 20 min or until the SEBS is completely dissolved in the solution.

After ink preparation, the flexible substrate for printing the fingerprint sensor is fabricated. With the assistance of a stainless-steel rod, a SIS layer of 1000 μm is formed on top of a plastic sheet of PET. The thin layer is dried at 60° C. for 30 min. The printed electrode patterns (Area of electrodes 0.02 $cm^2$) are designed in software and are transferred to stainless steel plates (12×12 $in^2$) etched to fabricate metallic stencils. The electrochemical system, composed of a working and reference electrodes, was screen printed using an MPM-SPM semi-automatic screen printer. The printing process consisted of printing first the reference electrode using the PEDOT:PSS ink on the SIS substrate followed by a curing step of 30 min at 120° C. Next, the working electrode was printed using the PEDOT:PSS-PB ink, similar drying conditions are applied after printing the electrode. Subsequently, the silver interconnection pattern was printed on top of the electrode system followed by a curing step of 15 min at 90° C. The interconnections are insulated using the SEBS resin. Finally, the insulator is allowed to dry for 10 min at 90° C. to obtain the printed IDE electrode.

The IDE electrodes are modified by drop-casting a mixture 6 μL of glucose oxidase (20 mg/mL in PBS 0.1 M pH 7.3) and 3 μL of glutaraldehyde (1% in DI water) on top of the exposed electrodes surfaces. After modification, the electrodes are stored overnight at 4° C. inside a refrigerator.

In-Vitro Sensor Characterization

The in-vitro characterization of the touch-based glucose sensor was conducted using both 0.1 M PBS (pH 7.3) and artificial sweat (AS, pH 6.0). Two-electrode cyclic voltammetry between −0.35 V and 0.55V was performed to observe a redox peak of PB molecules at 0.02 V and −0.08 V in PBS and 0.12 V and −0.04 V in AS. The optimization of the applying potential was studied at different potential decreasing from 0 V to −0.3 V with 50 mV steps. From the current response at different potential, −0.1 V was selected and used in subsequential in-vitro and on-body experiments (FIGS. 7A and 7B). Under optimized conditions, the glucose level was varied from 0 to 500 μM with 100 μM addition and showed good linearity towards in both PBS and AS (FIGS. 8A and 8B). Additionally, the selectivity test was performed in PBS followed by spiking 100 μM of glucose, lactic acid (LA), ascorbic acid (AA), acetaminophen (AP), and uric acid (UA)(FIG. 9).

On-Body Chemical Fingerprint Sensing

Fingerprint sensing was performed on healthy consenting individuals and in strict compliance with the protocol approved by the Institutional review board at the University of California, San Diego. Volunteers were asked to place their index fingers on top of the sensor for all on-body evaluations. The glucose levels were validated using a commercial blood glucose meter. Before using the sensor, volunteers were asked to clean their hands with water and soap. The on-body results were acquired using a benchtop Autolab potentiostat/galvanostat 204 from Metrohm. Chronoamperometric potential steps of −0.1 V of 30 s were used during all experiments. To collect blood glucose levels, the finger of each individual was pricked, and a small droplet of blood was analyzed. Afterward, fingertip glucose signals were measured by touching the sensor for 60 s. Next, two chronoamperometric steps were performed to quantify the current signal. The last current value from the second scan was taken as the corresponding sweat glucose level. After each sensing session, the sensor was firstly wetted with deionized water then gently wiped with paper tissue to dry for the next measurement.

Personalized Calibration on Body Experiment

Blood and fingertip glucose signals were acquired from five volunteers during 5 consecutive days in fasting state and 20 min after consuming sugar-rich food. The current and blood glucose values were plotted together and using a linear fitting, with a slope b and intercept a were acquired for each subject using data obtained from a given number of days. To obtain the predicted glucose concentration for each subject, the following formula is used:

$$BG = a + bi$$

where "i" represents the current value obtained after the second chronoamperometric scan.

Extended On-Body Experiments

Three subjects were recruited to perform 3-hour monitoring experiments. The fasting state glucose levels were recorded for 20 min, followed by meal consumption. After 90 min, a high-sugar content drink was provided to each subject. Simultaneously, blood and fingertip glucose were monitored every 10 and 5 min, respectively. Two subjects were recruited to perform 12-hour experiments. Experiments started by monitoring both blood and fingertip glucose every hour. The periodic monitoring of both parameters was changed only after meal consumption at 1, 5, and 10 h. of starting the experiment. At these times slots, blood, and fingertip glucose were monitored every 10 and 5 min, respectively.

Achieving strict glycemic control towards effective management of diabetes requires frequent or continuous measurements of glucose. Non-invasive glucose monitoring has always been regarded as the "holy grail" of next-generation biosensing technology owing to its tremendous impact on a large population and huge commercial market. Yet, after decades of development, diabetes patients, who rely on multiple blood glucose self-monitoring daily to prevent life-threatening complications, are still dependent on painful inconvenient finger-pricking glucometers and costly and invasive continuous glucose monitors (CGMs). Although sweat and interstitial fluid-based non-invasive glucose sensing technologies have been proposed, their practical implementation is yet limited due to their lengthy and complex biofluid extraction processes. Addressing these challenges, our group has recently explored the use of passive perspiration from the fingertip for chemical sensing due to its high natural sweat rate. This fingertip-based contact sensing uses hydrogel to extract sweat from the fingertip and enable chemical monitoring, and faces various limitations, such as analyte carry-over and dilution, solvent evaporation, and inconvenient gel placement and storage, that hinder its practical utility for tracking dynamically changing concentrations.

Addressing the above issues, the disclosed technology can be implemented in some embodiments to provide a reusable solid-state touch-based electrochemical sensing protocol for reliable, convenient frequent extended glucose monitoring. In addition, the disclosed technology can be implemented in some embodiments to provide a unique solid-state interdigitated electrode transducer for direct touch-based glucose monitoring without the need for any sweat-extraction mechanisms. When touched by the fingertip, the solid-state interface is rapidly covered by a sweat layer across the interdigitated electrode, which rapidly records the glucose level without any preconditioning or incubation. Such painless biosensor features reusability and speed, and therefore can greatly increase the testing frequency, compared to traditional finger pricking, towards extended tracking of dynamic glucose variations over the entire day. Unlike early studies based on stimulated sweating via exercise or iontophoresis, which reported a low correlation to blood glucose, the present use of natural perspiration offers high accuracy in predicting blood glucose levels in connection to a single first-day personalized calibration. Conducted over 160 trials on subjects with diverse backgrounds through multiple day-long glucose monitoring sessions, the sensor closely matches blood glucose temporal profiles, delivering highly accurate blood glucose concentration data, as indicated from a low mean absolute relative difference (MARD) of 8.15%, which compares favorably with the accuracy of commercial blood glucose strips and CGMs (typically 9-14%). With the attractive features of the new user-friendly non-invasive biosensing method and its high-quality data, the disclosed technology can be implemented in some embodiments to enable non-invasive glucose monitoring that can become an important component of diabetic self-care.

Figure 14:
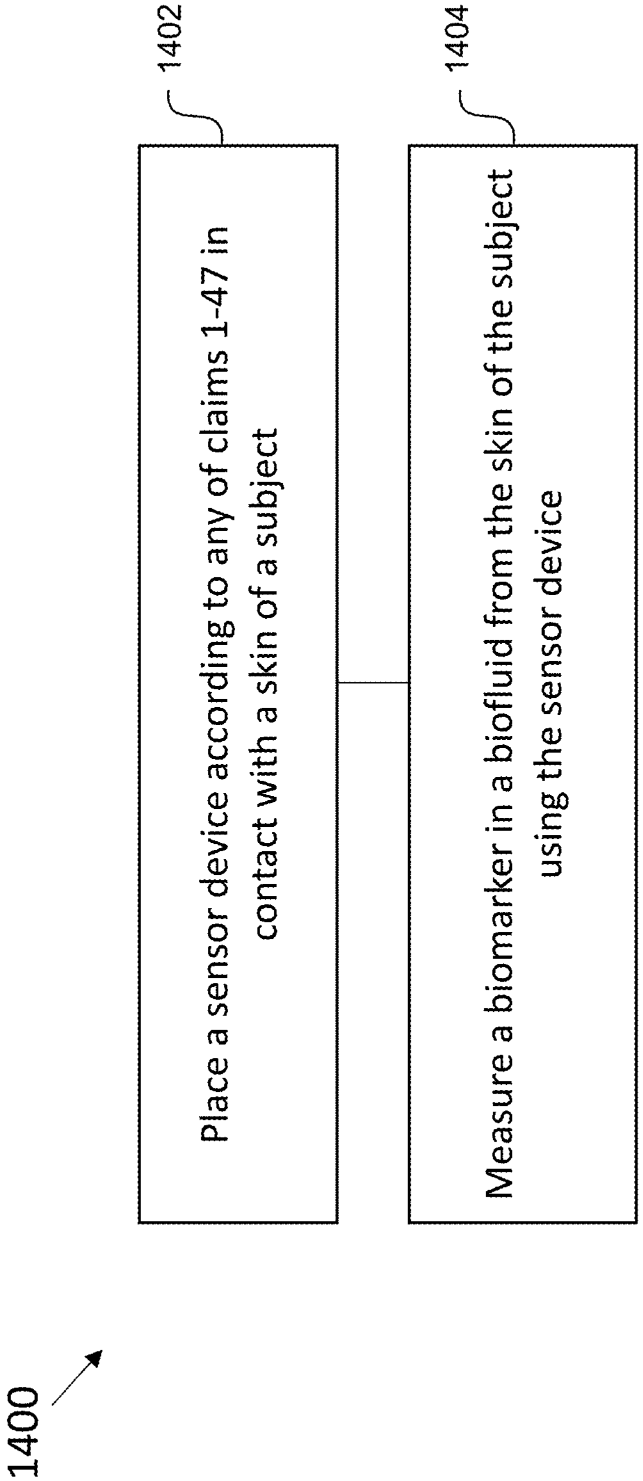
FIG. 14 shows an example method for measuring a biomarker in a biofluid based on some embodiments of the disclosed technology.

FIG. 14 shows an example method 1400 for measuring a biomarker in a biofluid based on some embodiments of the disclosed technology.

In some implementations, the method 1400 includes, at 1402, placing a sensor device in contact with a skin of a subject, and at 1404, measuring a biomarker in a biofluid from the skin of the subject using the sensor device. The sensor device may include a plurality of first electrodes and a plurality of second electrodes; a first current collector coupled to the plurality of first electrodes at one end of each first electrode; and a second current collector coupled to the plurality of second electrodes at one end of each second electrode, wherein the first electrodes and the second electrodes are alternately arranged, and adjacent first and second electrodes are spaced apart from each other by a predetermined distance.

Therefore, various implementations of features of the disclosed technology can be made based on the above disclosure, including the examples listed below.

Example 1. A sensor device, comprising: a substrate; a plurality of first electrodes and a plurality of second electrodes formed over the substrate; a first current collector formed over the substrate and coupled to the plurality of first electrodes at one end of each first electrode; and a second current collector formed over the substrate and coupled to the plurality of second electrodes at one end of each second electrode, wherein the first electrodes and the second electrodes are alternately arranged, and adjacent first and second electrodes are spaced apart from each other by a predetermined distance.

Example 2. The sensor device of example 1, wherein the plurality of first electrodes includes working electrodes, and the plurality of second electrodes includes reference or counter electrodes.

Example 3. The sensor device of example 1, wherein the plurality of first and second electrodes includes at least one of a metal, a carbonaceous material, a doped conductive metal oxide, a conductive polymer, or a metal salt.

Example 4. The sensor device of example 3, wherein the metal includes at least one of silver, gold, platinum, copper, titanium, or brass.

Example 5. The sensor device of example 3, wherein the carbonaceous material includes at least one of graphite, carbon-nanotubes, graphene, laser-induced graphene, glassy carbon, or reduced graphene oxide.

Example 6. The sensor device of example 3, wherein the doped conductive metal oxide includes indium-tin oxide (ITO).

Example 7. The sensor device of example 3, wherein the conductive polymer includes at least one of polyaniline, polypyrrole, polythiophene, or poly (3,4-ethylenedioxythiophene):polystyrene sulfonate (PEDOT:PSS).

Example 8. The sensor device of example 3, wherein the metal salt includes silver chloride.

Example 9. The sensor device of example 3, wherein the plurality of first and second electrodes includes an electroactive redox mediator that includes at least one of a quinone, a Prussian blue, an osmium-containing redox mediator, a ruthenium-containing mediator, an organic dye, tetrathiafulvalene, tetrathiafulvalene-tetracyanoquinodimethane, or ferrocene.

Example 10. The sensor device of example 9, wherein the quinone includes at least one of benzoquinone, naphthoquinone (NQ), anthraquinone, hydroquinone, or chlorohydroquinone.

Example 11. The sensor device of example 9, wherein the osmium-containing redox mediator includes the osmium-containing redox mediator includes osmium bipyridine.

Example 12. The sensor device of example 9, wherein the ruthenium-containing mediator includes ruthenium bipyridine.

Example 13. The sensor device of example 9, wherein the organic dye includes at least one of methylene blue, toluidine blue O, methylene green, azure A and B, or thionine.

Example 14. The sensor device of example 1, wherein the substrate includes a polymer substrate, and wherein the plurality of first and second electrodes includes one or more solid-state interdigitated electrodes (IDEs) deposited on the polymer substrate. In some implementations, the deposition can be performed using a planer deposition method. In some implementations, the first electrodes and the second electrodes include materials that are deposited onto the substrate using at least one of screen printing, inkjet printing, flexography, sputtering, lithography, electrodeposition, or direct ink writing.

Example 15. The sensor device of example 1, wherein the substrate includes at least one of glass, silicon, paper, textile, polymeric plastic or elastomer.

Example 16. The sensor device of example 15, wherein the substrate includes the polymeric plastic or the elastomer and comprises one or more polymer layers, wherein the one or more polymer layers includes at least one of polyethylene, polypropylene, polyethylene terephthalate, polyvinyl chloride, polystyrene, polysaccharide-based polymer, polystyrene-based block copolymer, polysaccharide, polyvinyl alcohol, or polyethylene vinyl acetate.

Example 17. The sensor device of example 16, wherein the polystyrene-based block copolymer includes at least one of polystyrene-polyethylene-polybutylene-polystyrene (SEBS), poly styrene-polyisoprene-polystyrene (SIS), or poly styrene-polybutylene-polystyrene (SBS)).

Example 18. The sensor device of example 16, wherein the polysaccharide includes at least one of starch polymer, cellulose, nitrocellulose, chitosan, ethylcellulose, or methylcellulose.

Example 19. The sensor device of example 1, wherein the substrate includes at least one of fluorinated polymer, co-polymer of the fluorinated polymer, poly (vinyl difluoroethylene), tetrafluoro propylene, or hexafluoro propylene.

Example 20. The sensor device of example 19, wherein the co-polymer of the fluorinated polymer includes poly (tetrafluoro ethylene).

Example 21. The sensor device of example 1, wherein the sensor device is structured to be placed directly onto skin surfaces to interact with a natural perspiration directly without a biofluid collection mechanism including microfluidics or hydrogels.

Example 22. The sensor device of example 21, wherein the biofluid includes a fingertip sweat.

Example 23. The sensor device of example 1, wherein the predetermined distance between the adjacent first and second electrodes includes ionic pathways for signal transduction when in contact with a skin surface of a user by natural perspiration, and wherein the ionic pathway is only constructed upon contact with the skin is eliminated upon removing the sensor from the skin surface.

Example 24. The sensor device of example 1, wherein the predetermined distance is smaller than 1 mm.

Example 25. The sensor device of example 1, wherein the plurality of first electrodes and the plurality of second electrodes are interdigitated with one another, and wherein the interdigitated electrodes arranged parallelly, radially, or concentrically.

Example 26. The sensor device of example 1, further comprising at least one of an enzymatic transduction layer or a non-enzymatic transduction layer formed over the first and second electrodes and the first and second current collectors to react selectively with a biomarker in a body fluid for detection.

Example 27. The sensor device of example 26, wherein the enzymatic transduction layer includes an enzymatic material that includes at least one of glucose oxidase, glucose dehydrogenase, lactate oxidase, lactate dehydrogenase, alcohol oxide, alcohol dehydrogenase, tyrosinase, ascorbate oxidase, urease, uricase, xanthine oxidase, tyrosinase, glutamate oxidase, laccase, hydroxybutyrate dehydrogenase, catalase, or bilirubin oxidase.

Example 28. The sensor device of example 26, wherein the non-enzymatic transduction layer includes an electroactive non-enzymatic material that includes at least one of a metal nanoparticle, a metal, a nanozyme, or an ion-selective material.

Example 29. The sensor device of example 28, wherein the metal nanoparticle includes at least one of gold nanoparticle, platinum nanoparticle, or silver nanoparticle.

Example 30. The sensor device of example 28, wherein the metal includes at least one of copper or nickel.

Example 31. The sensor device of example 28, wherein the ion-selective material includes at least one of hydrogen ionophores, sodium ionophores, potassium ionophores.

Example 32. The sensor devices of example 26, wherein the at least one of an enzymatic transduction layer or a non-enzymatic transduction layer includes at least one of an enzyme co-factor, or a cross-linking chemical deposited below, with, or above the at least one of an enzymatic transduction layer or a non-enzymatic transduction layer.

Example 33. The sensor device of example 32, wherein the enzyme co-factor includes at least one of nicotinamide adenine dinucleotide, flavin adenine dinucleotide, flavin mononucleotide, heme, or ascorbic acid.

Example 34. The sensor device of example 32, wherein the cross-linking chemical includes at least one of glutaraldehyde, epoxy, dihydrazide, bisacrylamide, 1-Ethyl-3-(3-dimethylaminopropyl)carbodiimide/N-hydroxysuccinimide (EDC/NHS)), stabilizer, polymer, or surfactant.

Example 35. The sensor device of example 34, wherein the stabilizer includes at least one of bovine serum albumin, human serum albumin, glycerol, or poly phenylenediamine.

Example 36. The sensor device of example 34, wherein the polymer includes at least one of polyethyleneimine, polyurethane, polyvinyl alcohol, polyvinyl pyrrolidone, chitosan, or Nafion.

Example 37. The sensor device of example 34, wherein the surfactant includes at least one of sodium dodecyl sulfate, sodium dodecyl styrene sulfonate, Triton X-100, Triton X-114, or Tween 80.

Example 38. The sensor device of example 1, further comprising: a signal transduction layer disposed over the first and second electrodes to functionalize the first and second electrodes for biomarkers; and a protection layer on the signal transduction layer to protect the signal transduction layer.

Example 39. The sensor device of example 38, wherein the protection layer includes at least one of Nafion, chitosan, polyethyleneimine, polyurethane, polyvinyl alcohol, polyvinyl chloride, poly (vinyl difluoroethylene), poly (tetrafluoro ethylene), tetrafluoro propylene, hexafluoro propylene, starch polymer, cellulose, nitrocellulose, chitosan, ethylcellulose, or methylcellulose.

Example 40. The sensor device of example 1, wherein the sensor device is configured to react selectively with a biomarker in a body fluid for detection, wherein the biomarker includes at least one of glucose, lactate, alcohol, levodopa, creatinine, urea, uric acid, bilirubin, hydroxybutyrate, vitamin, oxygen, ion, hormone, opioid, or cannabinoid.

Example 41. The sensor device of example 40, wherein the vitamin includes ascorbic acid.

Example 42. The sensor device of example 40, wherein the ion includes at least one of proton, sodium, potassium, chloride, fluoride, calcium, zinc, lead, cadmium, or mercury.

Example 43. The sensor device of example 40, wherein the hormone includes at least one of cortisol, adrenaline, or insulin.

Example 44. The sensor device of example 1, wherein the sensor device is integrated with an additional sensor for measuring physical parameters when in contact with a skin, wherein the physical parameters include at least one of temperature, moisture, or pressure.

Example 45. The sensor device of example 1, wherein the sensor device is integrated with an additional sensor for measuring physiological parameters when in contact with a skin, wherein the physiological parameters include blood oxygen levels, heart rate, fingerprint patterns, or blood pressure.

Example 46. A sensor device comprising a plurality of electrode arrays for simultaneous or sequential sensing of multiple biomarkers of physiological parameters, wherein each of the electrode arrays comprises: a plurality of first electrodes and a plurality of second electrodes; a first current collector coupled to the plurality of first electrodes at one end of each first electrode; and a second current collector coupled to the plurality of second electrodes at one end of each second electrode, wherein the first electrodes and the second electrodes are alternately arranged, and adjacent first and second electrodes are spaced apart from each other by a predetermined distance.

Example 47. An array of sensors including a plurality of sensor devices according to any of examples 1-46, wherein the plurality of sensor devices is formed onto a substrate for sensing multiple biomarkers in a biofluid from different locations of a body simultaneously or sequentially.

Example 48. A method, comprising: placing a sensor device according to any of examples 1-47 in contact with a skin of a subject; and measuring a biomarker in a biofluid from the skin of the subject using the sensor device.

Example 49. The method of example 48, wherein the biomarker includes at least one of glucose, lactate, alcohol, levodopa, creatinine, urea, uric acid, bilirubin, hydroxybutyrate, vitamin, oxygen, ion, hormone, opioid, or cannabinoid.

Example 50. The method of example 48, further comprising measuring at least one of a physical parameter or a physiological parameter together with the biomarker, wherein the physical parameter includes at least one of temperature, moisture, or pressure, and the physiological parameter includes at least one of skin resistance, temperature, blood oxygen levels, heart rate, fingerprint patterns, or blood pressure.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A glucose monitoring device for detecting glucose in a biofluid sample from a skin surface, the device comprising:

a) a substrate comprising a conductive layer;

b) a first electrode comprising a first electrode material deposited on the conductive layer, wherein the first electrode material comprises a transducer configured to generate an electrochemical signal from a reaction with the glucose from the biofluid sample; and c) a second electrode comprising a second electrode material deposited on the conductive layer, wherein the biofluid sample of the skin surface is collected by direct contact of a fingertip to the device, wherein the first electrode comprises a first plurality of digits and the second electrode comprises a second plurality of digits, wherein the first plurality of digits is alternately arranged with the second plurality of digits, and wherein the electrochemical signal is used to provide a blood glucose concentration of a user.

2. The device of claim 1, wherein the substrate comprises at least one of glass, silicon, paper, textile, polymer, or elastomer.

3. The device of claim 2, wherein the polymer comprises at least one of polyethylene, polypropylene, polyethylene terephthalate, polyvinyl chloride, polystyrene, polysaccharide-based polymer, polystyrene-based block copolymer, polysaccharide, polyvinyl alcohol, or polyethylene vinyl acetate.

4. The device of claim 1, wherein the conductive layer comprises a metal.

5. The device of claim 4, wherein the metal comprises platinum, silver, gold, copper, titanium, ruthenium, palladium, rhodium, brass, or a combination thereof.

6. The device of claim 1, wherein the reaction comprises a redox reaction.

7. The device of claim 1, wherein the transducer is glucose oxidase.

8. The device of claim 1, wherein the first electrode material comprises a cross-linker.

9. The device of claim 8, wherein the cross-linker comprises one or more of glutaraldehyde, epoxy, dihydrazide, bisacrylamide, 1-Ethyl-3-(3-dimethylaminopropyl) carbodiimide/N-hydroxysuccinimide (EDC/NHS)), stabilizer, polymer, or surfactant.

10. The device of claim 1, wherein the second electrode material comprises a redox mediator.

11. The device of claim 10, wherein the redox mediator comprises an iron-based redox couple.

12. The device of claim 1, wherein the second electrode material comprises a conductive polymer.

13. The device of claim 12, wherein the conductive polymer comprises one or more of polyaniline, polypyrrole, polythiophene, or poly (3,4-ethylenedioxythiophene):polystyrene sulfonate (PEDOT:PSS).

14. The device of claim 1, wherein the first and second plurality of digits are separated by a predetermined distance of about 1 mm or less.

15. The device of claim 1, wherein the alternately arranged first and second plurality of digits are interdigitated.

16. The device of claim 1, wherein a contact time of the fingertip to the device is about 30 s to about 60 s.

17. The device of claim 16, wherein the biofluid comprises sweat.

18. The device of claim 1, wherein the device comprises a second layer, wherein the second layer comprises one or more of chitosan, agarose, or polyethyleneimine.

19. The device of claim 1, wherein the device comprises a third layer, wherein the third layer comprises one or more of Nafion or cellulosic material.

20. The device of claim 1, wherein the device comprises a protection layer, wherein the protection layer comprises one or more of Nafion, polyethyleneimine, polyurethane, polyvinyl alcohol, polyvinyl chloride, poly (vinyl difluoroethylene), poly (tetrafluoro ethylene), tetrafluoro propylene, hexafluoro propylene, starch polymer, cellulose, nitrocellulose, chitosan, ethylcellulose, or methylcellulose.

* * * * *